United States Patent
Gent et al.

(10) Patent No.: US 11,891,357 B2
(45) Date of Patent: Feb. 6, 2024

(54) PROCESS TO PRODUCE ETHYLENE AND VINYL ACETATE MONOMER AND DERIVATIVES THEREOF

(71) Applicant: NOVA Chemicals (International) S.A., Fribourg (CH)

(72) Inventors: David Gent, Red Deer (CA); Shahin Goodarznia, Calgary (CA); Vasily Simanzhenkov, Calgary (CA); Kamal Serhal, Calgary (CA); Claire Ennis, Calgary (CA); Robert Ladd, Airdrie (CA)

(73) Assignee: NOVA Chemicals (International) S.A., Fribourg (CH)

( * ) Notice: Subject to any disclaimer, the term of this patent is extended or adjusted under 35 U.S.C. 154(b) by 559 days.

(21) Appl. No.: 16/977,601

(22) PCT Filed: Mar. 8, 2019

(86) PCT No.: PCT/IB2019/051919
§ 371 (c)(1),
(2) Date: Sep. 2, 2020

(87) PCT Pub. No.: WO2019/175732
PCT Pub. Date: Sep. 19, 2019

(65) Prior Publication Data
US 2021/0040018 A1 Feb. 11, 2021

Related U.S. Application Data

(60) Provisional application No. 62/743,775, filed on Oct. 10, 2018, provisional application No. 62/741,705, (Continued)

(51) Int. Cl.
*C07C 5/48* (2006.01)
*B01J 19/24* (2006.01)
(Continued)

(52) U.S. Cl.
CPC ............... *C07C 5/48* (2013.01); *B01J 19/245* (2013.01); *B01J 21/08* (2013.01); *B01J 23/26* (2013.01);
(Continued)

(58) Field of Classification Search
USPC .......................................................... 526/75
See application file for complete search history.

(56) References Cited

U.S. PATENT DOCUMENTS

| | | | |
|---|---|---|---|
| 2,468,923 | A | 5/1949 | Cornthwaite et al. |
| 3,419,654 | A | 12/1968 | Teiichiro et al. |

(Continued)

FOREIGN PATENT DOCUMENTS

| | | | | |
|---|---|---|---|---|
| CA | 1333721 | | 12/1994 | |
| CA | 2465380 | A1 * | 4/2004 | ............ C07C 67/05 |

(Continued)

OTHER PUBLICATIONS

[No author listed], "Chemical Process," Research Disclosure 338030, Jun. 1992, 7 pages.
(Continued)

*Primary Examiner* — Fred M Teskin
(74) *Attorney, Agent, or Firm* — Fish & Richardson P.C.

(57) ABSTRACT

A method that includes (a) providing a stream containing ethane and oxygen to an ODH reactor; (b) converting a portion of the ethane to ethylene and acetic acid in the ODH reactor to provide a stream containing ethane, ethylene, acetic acid, oxygen and carbon monoxide; (c) separating a portion of the acetic acid from the stream to provide an acetic acid stream and a stream containing ethane, ethylene, oxygen and carbon monoxide; (d) providing the stream to a CO Oxidation Reactor containing a catalyst that includes a group 11 metal to convert carbon monoxide to carbon dioxide and reacting acetylene to produce a stream contain-
(Continued)

ing ethane, ethylene and carbon dioxide; and (e) providing a portion of the stream and a portion of the acetic acid stream to a third reactor containing a catalyst that includes a metal selected from group 10 and group 11 metals to produce vinyl acetate.

28 Claims, 11 Drawing Sheets

Related U.S. Application Data filed on Oct. 5, 2018, provisional application No. 62/642,265, filed on Mar. 13, 2018.

(51) Int. Cl.
| | | |
|---|---|---|
| *B01J 21/08* | (2006.01) | |
| *B01J 23/26* | (2006.01) | |
| *B01J 23/34* | (2006.01) | |
| *B01J 23/656* | (2006.01) | |
| *B01J 23/66* | (2006.01) | |
| *C07C 5/09* | (2006.01) | |
| *C07C 67/05* | (2006.01) | |
| *C08F 10/02* | (2006.01) | |
| *B01J 23/83* | (2006.01) | |

(52) U.S. Cl.
CPC .......... *B01J 23/34* (2013.01); *B01J 23/6565* (2013.01); *B01J 23/66* (2013.01); *B01J 23/83* (2013.01); *C07C 5/09* (2013.01); *C07C 67/05* (2013.01); *C08F 10/02* (2013.01); *B01J 2219/0004* (2013.01); *C07C 2521/08* (2013.01); *C07C 2523/26* (2013.01); *C07C 2523/34* (2013.01); *C07C 2523/656* (2013.01); *C07C 2523/66* (2013.01); *C07C 2523/83* (2013.01)

(56) References Cited

U.S. PATENT DOCUMENTS

| | | | |
|---|---|---|---|
| 5,185,308 | A | 2/1993 | Bartley et al. |
| 5,500,198 | A | 3/1996 | Liu et al. |
| 6,852,877 | B1 † | 2/2005 | Zeyss |
| 7,468,455 | B2 | 12/2008 | Mazanec et al. |
| 8,642,825 | B2 | 2/2014 | Kustov et al. |
| 8,846,996 | B2 | 9/2014 | Kustov et al. |
| 8,993,796 | B2 | 3/2015 | Rinne et al. |
| 9,545,610 | B2 | 1/2017 | Simanzhenkov et al. |
| 9,550,709 | B2 | 1/2017 | Simanzhenkov et al. |
| 9,573,877 | B2 | 2/2017 | Vismans et al. |
| 9,963,412 | B2 | 5/2018 | Bos et al. |
| 9,993,798 | B2 | 6/2018 | Simanzhenkov et al. |
| 10,017,432 | B2 | 7/2018 | Bos et al. |
| 10,343,957 | B2 | 7/2019 | Serhal et al. |
| 2006/0142508 | A1 † | 6/2006 | Shamshoum |
| 2008/0132723 | A1 † | 6/2008 | Johnson |
| 2017/0050178 | A1 | 2/2017 | Simanzhenkov et al. |
| 2018/0009662 | A1 | 1/2018 | Simanzhenkov et al. |
| 2020/0002251 | A1 † | 1/2020 | Mitkidis |

FOREIGN PATENT DOCUMENTS

| | | |
|---|---|---|
| DE | 295506 | 11/1991 |
| EP | 0330853 | 7/1993 |
| GB | 1559540 | 1/1980 |
| WO | WO 1999/08791 | 2/1999 |
| WO | WO 2003/055838 | 7/2003 |
| WO | 2010115108 A1 † | 10/2010 |
| WO | 2017/046315 A1 | 3/2017 |
| WO | 2017/072086 A1 | 5/2017 |
| WO | 2017/144584 A1 | 8/2017 |
| WO | 2018/019760 A1 | 2/2018 |
| WO | 2018/024650 A1 | 2/2018 |

OTHER PUBLICATIONS

International Preliminary Report on Patentability in International Appln. No. PCT/IB2019/051919, dated Sep. 15, 2020, 8 pages.
International Search Report and Written Opinion in International Appln. No. PCT/IB2019/051919, dated Jun. 17, 2019, 12 pages.
Mamontov, G.V.; Gorbunova, A.S.; Vyshegorodsteva, E.V.; Zaikovskii, V.I.; Vodyankina, O.V.; Selective oxidation of CO in the presence of propylene over Ag/MCM-41 catalyst; Catalysis Today (2019); 333—pp. 245-250.
Mamontov, G.V.; Grabchenko, M.V.; Litvyakova, N.N.; Gorbunova, A.S.; Dutov, V.V.; Zaikovskii, V.I.; Vodyankina, O.V.; Selective oxidation of CO in the presence of propylene over AG/SiO2 catalysts; 8th World Congress on Oxidation Catalysis & XII European Workshop Meeting in Innovation in Selective Oxidation Catalysis (ISO'17), Sep. 3-8, 2017, Krakow, Poland—Book of Abstracts, p. 111.

\* cited by examiner
† cited by third party

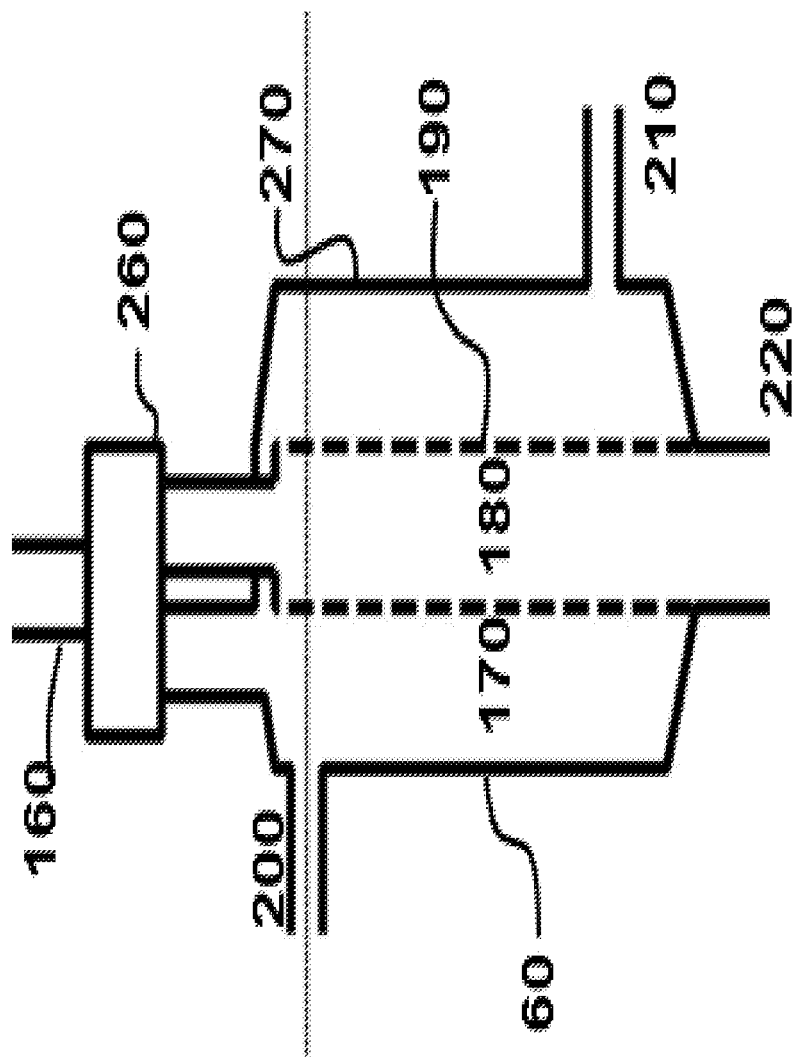

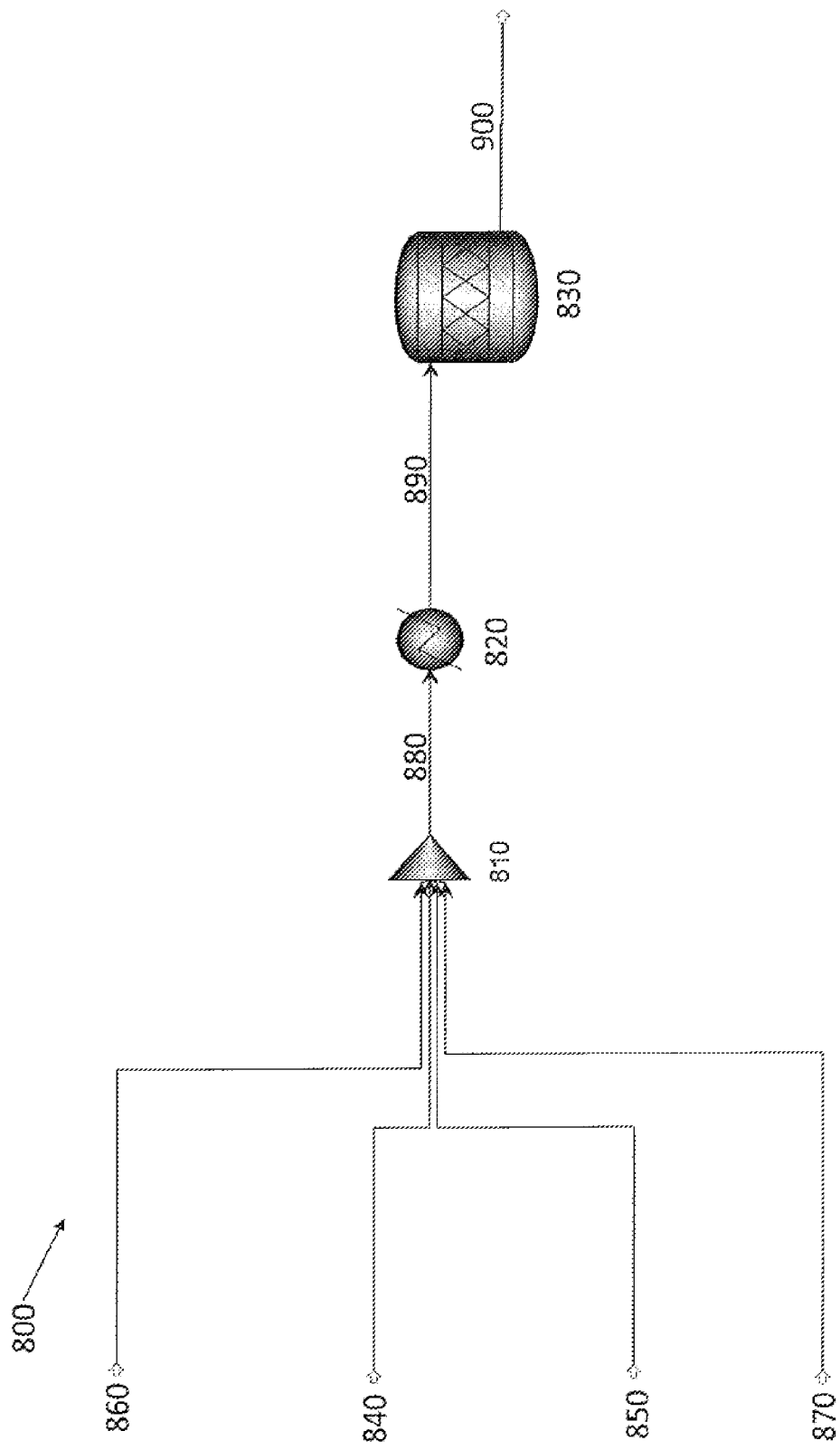

PROCESS TO PRODUCE ETHYLENE AND VINYL ACETATE MONOMER AND DERIVATIVES THEREOF

The present disclosure relates generally to oxidative dehydrogenation (ODH) of ethane into ethylene with subsequent reaction of at least a portion of the ethylene with acetic acid to provide vinyl acetate monomer.

Olefins like ethylene, propylene, and butylene, are basic building blocks for a variety of commercially valuable polymers. Since naturally occurring sources of olefins do not exist in commercial quantities polymer producers rely on methods for converting the more abundant lower alkanes into olefins. The method of choice for today's commercial scale producers is steam cracking, a highly endothermic process where steam-diluted alkanes are subjected very briefly to a temperature of at least 800° C. The fuel demand to produce the required temperatures and the need for equipment that can withstand that temperature add significantly to the overall cost. Also, the high temperature promotes the formation of coke which accumulates within the system, resulting in the need for costly periodic reactor shut-down for maintenance and coke removal.

Oxidative dehydrogenation (ODH) is an alternative to steam cracking that is exothermic and produces little or no coke. In ODH a lower alkane, such as ethane, is mixed with oxygen in the presence of a catalyst and optionally an inert diluent, such as carbon dioxide or nitrogen, in some embodiments at temperatures as low as 300° C., to produce the corresponding alkene. In some embodiments, various other oxidation products, most notably carbon dioxide and acetic acid may also be produced in this process. In some embodiments ODH suffers from lower conversion rates when compared to steam cracking, a fact that when combined with lower selectivity and the risk of thermal explosion due to mixing of a hydrocarbon with oxygen, may have prevented ODH from achieving widespread commercial implementation.

Vinyl acetate can be prepared in the gas phase from ethylene, acetic acid and oxygen or oxygen-containing gases as described, for example, in Canadian Patent No. 1,333, 721; WO 99/08791; U.S. Pat. No. 5,185,308 and GB 1 559 540. In these processes, it is known that carbon monoxide can act as a poison to the vinyl acetate monomer catalyst when present at even low levels. However, an effect means of removing carbon monoxide is not disclosed.

BRIEF DESCRIPTION OF DRAWINGS

FIG. 6D—Schematic of embodiment of oxygen separation module where C1 hydrocarbon containing line can be directed to either of or both the permeate side and the retentate side.

FIG. 8—is a block diagram showing the process described in Example 7.

Figure 1:
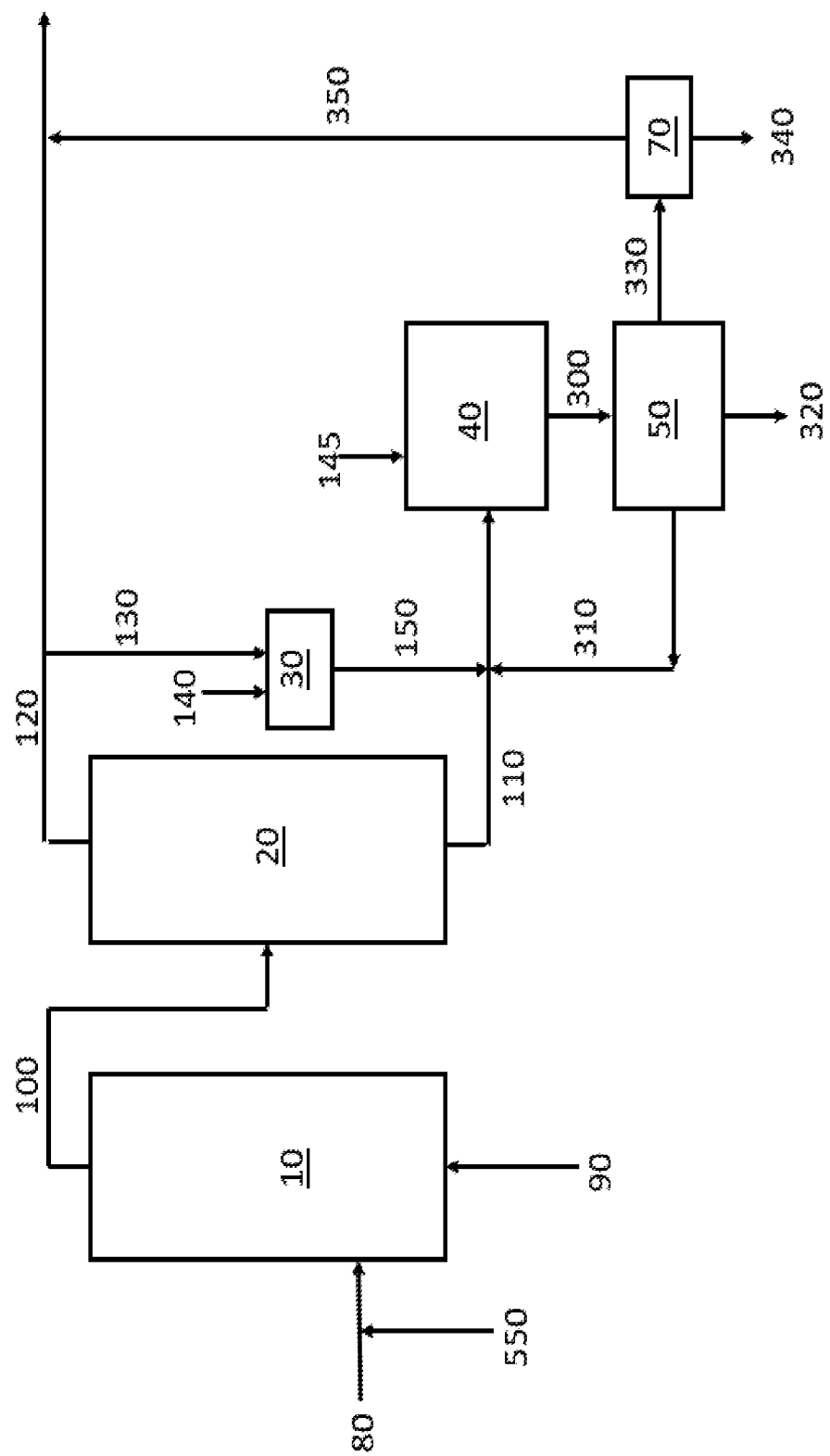
FIG. 1 is a graphic depiction of portions of a chemical complex according to some embodiments of the disclosure.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the desired properties, which the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

As used herein, the term "alkane" refers to an acyclic saturated hydrocarbon. In many cases, an alkane consists of hydrogen and carbon atoms arranged in a linear structure in which all of the carbon-carbon bonds are single bonds. Alkanes have the general chemical formula $C_nH_{2n+2}$. In many embodiments of the disclosure, "alkane" refers to one or more of ethane, propane, butane, pentane, hexane, octane, decane and dodecane. In particular embodiments, alkanes refer to ethane and propane and, in some embodiments, ethane.

As used herein, the term "alkene" refers to unsaturated hydrocarbons that contains at least one carbon-carbon double bond. In many embodiments, "alkenes" refer to alpha olefins. In many embodiments of the disclosure, "alkenes" refer to one or more of ethylene, propylene, 1-butene, butadiene, pentene, pentadiene hexene, octene, decene and dodecene. In particular embodiments, "alkenes" refer to ethylene and propylene and, in some embodiments, ethylene.

As used herein, the terms "alpha olefin" or "α-olefin" refer to a family of organic compounds which are alkenes (also known as olefins) with a chemical formula $C_xH_{2x}$, distinguished by having a double bond at the primary or alpha (α) position. In many embodiments of the disclosure, "alpha olefin" refers to one or more of ethylene, propylene, 1-butene, 1-pentene, 1-hexene, 1-octene, 1-decene and 1-dodecene. In particular embodiments, "alpha olefins" refer to ethylene and propylene and, in some embodiments, ethylene.

As used herein, the term "essentially free of oxygen" means the amount of oxygen present, if any, remaining in a process stream after the one or more ODH reactors, and in many embodiments after the CO Oxidation Reactor as described herein, is low enough that it will not present a flammability or explosive risk to the downstream process streams or equipment.

As used herein, the term "fixed bed reactor" refers to one or more reactors, in series or parallel, often including a cylindrical tube filled with catalyst pellets with reactants flowing through the bed and being converted into products. The catalyst in the reactor may have multiple configuration including, but not limited to, one large bed, several horizontal beds, several parallel packed tubes, multiple beds in their own shells.

As used herein, the term "fluidized bed reactor" refers to one or more reactors, in series or parallel, often including a fluid (gas or liquid) which is passed through a solid granular catalyst, which can be shaped as tiny spheres, at high enough velocities to suspend the solid and cause it to behave as though it were a fluid.

As used herein, the term "gas phase polyethylene process" refers to a process where a mixture of ethylene, optional alpha olefin comonomers and hydrogen is passed over a catalyst in a fixed or fluidized bed reactor. The ethylene and optional alpha olefins polymerize to form grains of polyethylene, suspended in the flowing gas, which can pass out of the reactor. In some embodiments, two or more of the individual reactors are placed in parallel or in series, each of which are under slightly different conditions, so that the properties of different polyethylenes from the reactors are present in the resulting polyethylene blend. In many cases the catalyst system includes, but is not limited to, chromium catalysts, Ziegler-Natta catalysts, zirconocene catalysts, and metallocene catalysts and combinations thereof.

As used herein, the term "HDPE" refers to high density polyethylene, which generally has a density of greater or equal to 0.941 g/cm3. HDPE has a low degree of branching. HDPE is often produced using chromium/silica catalysts, Ziegler-Natta catalysts or metallocene catalysts.

As used herein, the term "high pressure polyethylene process" refers to converting ethylene gas into a white solid by heating it at very high pressures in the presence of minute quantities of oxygen (about <10 ppm oxygen) at about 1000-3000 bar and at about 80-300° C. In many cases, the high pressure polyethylene process produces LDPE.

As used herein, the term "LDPE" refers to low density polyethylene, which is a polyethylene with a high degree of branching with long chains. Often, the density of a LDPE will range from 0.910 to 0.940 g/cm³. LDPE is created by free radical polymerization.

As used herein, the term "LLDPE" refers to linear low density polyethylene, which is a polyethylene that can have significant numbers of short branches resulting from copolymerization of ethylene with at least one α-olefin comonomer. In some cases, LLDPE has a density in the range of 0.915 to 0.925 g/cm³. In many cases, the LLDPE is an ethylene hexene copolymer, ethylene octene copolymer or ethylene butene copolymer. The amount of comonomer incorporated can be from 0.5 to 12 mole %, in some cases, from 1.5 to 10 mole %, and, in other cases, from 2 to 8 mole % relative to ethylene.

As used herein, the term "long-chain branching" refers to a situation where during α-olefin polymerization, a vinyl terminated polymer chain is incorporated into a growing polymer chain. Long branches often have a length that is longer than the average critical entanglement distance of a linear (no long chain branching) polymer chain. In many cases long chain branching effects melt rheological behavior.

As used herein, the term "low pressure polyethylene process" refers to polymerizing ethylene using a catalyst that in many cases includes aluminum at generally lower pressures than the high pressure polyethylene process. In many cases, the low pressure polyethylene process is carried out at about 10 to 80 bar and at about 70 to 300° C. In many cases, the low pressure polyethylene process provides HDPE. In particular cases, an α-olefin comonomer is included in the low pressure polyethylene process to provide LLDPE.

As used herein, the term "MDPE" refers to medium density polyethylene, which is a polyethylene with some short and/or long chain branching and a density in the range of 0.926 to 0.940 g/cm³. MDPE can be produced using chromium/silica catalysts, Ziegler-Natta catalysts or metallocene catalysts.

As used herein, the term "monomer" refers to small molecules containing at least one double bond that reacts in the presence of a free radical polymerization initiator to become chemically bonded to other monomers to form a polymer.

As used herein, the term "moving bed reactor" refers to reactors in which the catalytic material flows along with the reactants and is then separated from the exit stream and recycled.

As used herein, the term "MoVOx catalyst" refers to a mixed metal oxide having the empirical formula $Mo_{6.5-7.0}V_3O_d$, where d is a number to satisfy the valence of the oxide; a mixed metal oxide having the empirical formula $Mo_{6.25-7.25}V_3O_d$, where d is a number to satisfy the valence of the oxide, or combinations thereof.

As used herein, the term, "olefinic monomer" includes, without limitation, α-olefins, and in particular embodiments ethylene, propylene, 1-butene, 1-hexene, 1-octene and combinations thereof.

As used herein, the term, "oxidative dehydrogenation" or "ODH" refers to processes that couple the endothermic dehydration of an alkane with the strongly exothermic oxidation of hydrogen as is further described herein.

As used herein, the term "polyolefin" refers to a material, which is prepared by polymerizing a monomer composition containing at least one olefinic monomer.

As used herein, the term "polyethylene" includes, without limitation, homopolymers of ethylene and copolymers of ethylene and one or more α-olefins.

As used herein, the term "polypropylene" includes, without limitation, homopolymers of propylene, including isotactic polypropylene and syndiotactic polypropylene and copolymers of propylene and one or more α-olefins.

As used herein, the term "polymer" refers to macromolecules composed of repeating structural units connected by covalent chemical bonds and is meant to encompass, without limitation, homopolymers, random copolymers, block copolymers and graft copolymers.

As used herein, "polyvinyl acetate" refers to a synthetic resin prepared by the polymerization of a monomer mixture that includes at least 50 weight percent, and in some cases 100 weight percent vinyl acetate monomer.

As used herein, "polyvinyl alcohol" refers to a synthetic resin where some or all of the vinyl acetate derived repeat units in polyvinyl acetate are subjected to a hydrolysis, or "alcoholysis" reaction that removes the acetate groups from vinyl acetate derived repeat units without disrupting the long-chain structure of the polymer. The chemical structure of the resulting vinyl alcohol repeating units is:

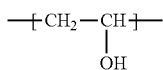

As used herein "polyvinyl butyral" or "PVB" refers to a polymer prepared by reacting polyvinyl alcohol with butyraldehyde resulting, in many cases, in a polymer that includes repeat units having the following structure:

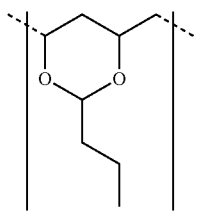

As used herein, the term "short chain branching" refers to copolymers of ethylene with an α-olefin or with branches of less than about 40 carbon atoms. In many cases, the α-olefin or branches are present at less than 20 wt. %, in some cases less than 15 wt. % of the polyethylene. In many cases, the presence of short chain branches interferes with the formation of the polyethylene crystal structure and is observed as a lower density compared with a linear (no short chain branching) polyethylene of the same molecular weight.

As used herein, the term "solution polyethylene process" refers to processes that polymerize ethylene and one or more optional α-olefins in a mixture of lower alkane hydrocarbons in the presence of one or more catalysts. In some embodiments, two or more of the individual reactors are placed in parallel or in series, each of which can be under slightly different conditions, so that the properties of different polyethylenes from the reactors are present in the resulting polyethylene blend. In many cases the catalysts include, but are not limited to, chromium catalysts, Ziegler-Natta catalysts, zirconocene catalysts, hafnocene catalysts, phosphinimine catalysts and metallocene catalysts and combinations thereof.

As used herein, the term "slurry polyethylene process" refers to single-tube loop reactors, double-tube loop reactors or autoclaves (stirred-tank reactors) used to polymerize ethylene and optional α-olefins in the presence of a catalyst system and a diluent. Non-limiting examples of diluents include isobutane, n-hexane or n-heptane. In some embodiments, two or more of the individual reactors are placed in parallel or in series, each of which can be under slightly different conditions, so that the properties of different polyethylenes from the reactors are present in the resulting polyethylene blend. In many cases the catalyst system includes, but is not limited to, chromium catalysts, Ziegler-Natta catalysts, zirconocene catalysts, hafnocene catalysts, phosphinimine catalysts and metallocene catalysts and combinations thereof.

As used herein, the term "substantially free of acetylene" means the amount of acetylene present, if any, remaining in a process stream after the one or more ODH reactors, and in many embodiments after the CO Oxidation reactor as described herein, is undetectable using the analytical techniques described herein or zero vppm.

As used herein, the term "swing bed type reactor arrangement" is a gas phase reactor system where a first vessel effectively operates as a reactor and a second vessel effectively operates as a regenerator for regenerating the catalyst system. This arrangement can be used with fixed bed as well as fluidized bed gas phase polyethylene reactors.

As used herein, the term "thermoplastic" refers to a class of polymers that soften or become liquid when heated and harden when cooled. In many cases, thermoplastics are high-molecular-weight polymers that can be repeatedly heated and remolded. In many embodiments of the disclosure, thermoplastic resins include polyolefins and elastomers that have thermoplastic properties.

As used herein, the terms "thermoplastic elastomers" and "TPE" refer to a class of copolymers or a blend of polymers (in many cases a blend of a thermoplastic and a rubber) which includes materials having both thermoplastic and elastomeric properties.

As used herein, the terms "thermoplastic olefin" or "TPO" refer to polymer/filler blends that contain some fraction of polyethylene, polypropylene, block copolymers of polypropylene, rubber, and a reinforcing filler. The fillers can include, without limitation, talc, fiberglass, carbon fiber, wollastonite, and/or metal oxy sulfate. The rubber can include, without limitation, ethylene-propylene rubber, EPDM (ethylene-propylene-diene rubber), ethylene-butadiene copolymer, styrene-ethylene-butadiene-styrene block copolymers, styrene-butadiene copolymers, ethylene-vinyl acetate copolymers, ethylene-alkyl (meth)acrylate copolymers, very low density polyethylene (VLDPE) such as those available under the Flexomer® resin trade name from the Dow Chemical Co., Midland, MI, styrene-ethylene-ethylene-propylene-styrene (SEEPS). These can also be used as the materials to be modified by the interpolymer to tailor their rheological properties.

As used herein, the terms "vinyl acetate", "vinyl acetate monomer" and "yAM" refer to polymerizable molecules generally conforming to the structure $CH_2=CHCO_2CH_3$.

As used herein, the term "VLDPE" refers to very low density polyethylene, which is a polyethylene with high levels of short chain branching with a typical density in the range of 0.880-0.915 g/cc. In many cases VLDPE is a substantially linear polymer. VLDPE is typically produced by copolymerization of ethylene with α-olefins. VLDPE is often produced using metallocene catalysts.

Unless otherwise specified, all molecular weight values are determined using gel permeation chromatography (GPC). Molecular weights are expressed as polyethylene equivalents with a relative standard deviation of about 2.9% for the number average molecular weight ("Mn") and about 5.0% for the weight average molecular weight ("Mw"). Unless otherwise indicated, the molecular weight values indicated herein are weight average molecular weights (Mw).

In some embodiments disclosed herein, the degree to which carbon monoxide is produced during the ODH process can be mitigated by converting it to carbon dioxide, which can then act as an oxidizing agent. The process can be manipulated so as to control the output of carbon dioxide from the process to a desired level. Using the methods described herein a user may choose to operate in carbon dioxide neutral conditions such that surplus carbon dioxide need not be flared or released into the atmosphere.

Disclosed herein are methods for mitigating carbon monoxide and/or acetylene in an ODH process and controlling the carbon dioxide output from the ODH process. Aspects of the methods include introducing, into at least one ODH reactor a gas mixture of a lower alkane, oxygen and carbon dioxide, under conditions that allow production of the corresponding alkene and smaller amounts of various by-products. For multiple ODH reactors, each reactor contains the same or different ODH catalyst, provided, in some embodiments, the at least one ODH catalyst is capable of using carbon dioxide as an oxidizing agent. In some embodiments steam or other inert diluents may also be introduced into the reactor as part of the gas mixture. In some embodiments the amount of carbon dioxide leaving the reactor is subsequently monitored. If the amount of carbon dioxide output is below a desired level then the amount of steam introduced into the reactor can be increased. If the amount of carbon dioxide output is above the desired level then the amount of steam introduced into the reactor can be decreased.

In some embodiments the lower alkane is ethane, and the corresponding alkene is ethylene.

Particular aspects of the disclosure are directed to when the lower alkane is ethane and the corresponding alkene is ethylene. These aspects are directed to methods of converting ethane to ethylene and combining at least a portion of the ethylene with acetic acid to form vinyl acetate. The method according to these aspects includes (a) providing a first stream that includes ethane and oxygen to an oxidative dehydrogenation reactor; (b) converting at least a portion of the ethane to ethylene and acetic acid in the oxidative dehydrogenation reactor to provide a second stream exiting the oxidative dehydrogenation reactor that includes ethane, ethylene, acetic acid, oxygen and carbon monoxide; (c) separating at least a portion of the acetic acid from the second stream to provide an acetic acid containing stream and a third stream that includes ethane, ethylene, oxygen and carbon monoxide; (d) providing the third stream to a CO Oxidation Reactor containing a catalyst that includes a group 11 metal and optionally a promoter that includes $CeO_2$, $ZrO_2$ and combinations thereof to convert a least a portion of the carbon monoxide to carbon dioxide to produce a fourth stream that includes ethane, ethylene and carbon dioxide; and (e) providing a portion of the fourth stream and at least a portion of the acetic acid containing stream to a third reactor containing a catalyst that includes a metal selected from the group 10 and group 11 metals and combinations thereof to convert a least a portion of the ethylene and acetic acid to vinyl acetate.

In further embodiments, at least one ODH reactor is a fixed bed reactor. In some embodiments at least one ODH reactor is a fixed bed reactor that includes heat dissipative particles within the fixed bed. In some embodiments the heat dissipative particles have a thermal conductivity that is greater than the catalyst. In alternative embodiments, at least one ODH reactor is a fluidized bed reactor.

In some embodiments, at least one ODH catalyst is a mixed metal oxide catalyst. In particular embodiments, at least one ODH catalyst is a mixed metal oxide of the formula: $Mo_aV_bTe_cNb_dPd_eO_f$, wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to satisfy the valence state of the catalyst.

In other particular embodiments, at least one ODH catalyst is a mixed metal oxide of the formula:

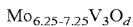

$$Mo_{6.25-7.25}V_3O_d$$

where d is a number to satisfy the valence of the oxide.

Various embodiments relate to oxidative dehydrogenation (ODH) of lower alkanes into corresponding alkenes. Lower alkanes are saturated hydrocarbons with from 2 to 4 carbons, and the corresponding alkene includes hydrocarbons with the same number of carbons, but with one carbon to carbon double bond. While any of the lower alkanes can be converted to their corresponding alkenes using the methods disclosed herein, one particular embodiment is the ODH of ethane, producing its corresponding alkene, ethylene.

Carbon Dioxide Output

Carbon dioxide can be produced in the ODH reaction as a by-product of oxidation of the alkanes and recycled from the oxidation of carbon monoxide. Carbon dioxide can also be added into the ODH reactor when used as an inert diluent. Conversely, carbon dioxide may be consumed when it acts as an oxidant for the dehydrogenation reaction. The carbon dioxide output is therefore a function of the amount of carbon dioxide added and produced minus that consumed in the oxidative process. In some embodiments, the disclosed methods control the degree to which carbon dioxide acts as an oxidizing agent so as to impact the overall carbon dioxide output coming off the ODH reactor.

Measuring the amount of carbon dioxide coming off the ODH reactor can be done using any means known in the art. For example, one or more detectors such as GC, IR, or Rahman detectors, are situated immediately downstream of the reactor to measure the carbon dioxide output. While not required, the output of other components may also be measured. These include but are not limited to the amounts of ethylene, unreacted ethane, carbon monoxide and oxygen, and by-products such as acetic acid. Also, it should be noted that depending on the chosen metric for carbon dioxide output, the output levels of the other components, for example ethane, may actually be required.

Carbon dioxide output can be stated using any metric commonly used in the art. For example, the carbon dioxide output can be described in terms of mass flow rate (g/min) or volumetric flow rate ($cm^3$/min). In some embodiments, normalized selectivity can be used to assess the degree to which carbon dioxide is produced or consumed. In that instance, the net mass flow rate of $CO_2$—the difference between the mass flow rate of $CO_2$ entering and leaving the ODH reactor—is normalized to the conversion of ethane, in essence describing what fraction of ethane is converted into carbon dioxide as opposed to ethylene, or other by-products such as acetic acid. A carbon selectivity of 0 indicates that the amount of carbon dioxide entering the reactor is the same as the carbon dioxide output. In other words, the process is carbon dioxide neutral. A positive carbon dioxide selectivity alerts a user that carbon dioxide is being produced, and that any oxidation of carbon dioxide that is occurring is insufficient to offset that production, resulting in the process being carbon dioxide positive which may result in a lower selectivity for the olefin.

In some embodiments, the methods and apparatus disclosed herein provide the possibility of a carbon dioxide negative process. In this instance, carbon dioxide is oxidized at a higher rate than it is produced and shows a negative carbon selectivity. The ODH process may produce carbon dioxide, but the degree to which carbon dioxide is consumed while acting as an oxidizing agent offsets any production that is occurring. Many industrial processes, in addition to ODH, produce carbon dioxide which must be captured or flared where it contributes to the emission of greenhouse gases. When using a carbon dioxide negative process, the excess carbon dioxide from other processes may be captured and used as the inert diluent in the ODH process under conditions where there is negative carbon selectivity. An advantage then is the ability to reduce the amount of carbon dioxide produced in the ODH process in combination with other processes, such as thermal cracking. In addition, oxidation of carbon dioxide is endothermic and by increasing the degree to which carbon dioxide acts as an oxidizing agent, heat produced from ODH of ethane is partially offset by oxidation of carbon dioxide, reducing the degree to which heat must be removed from the reactor. In some embodiments, when acting as an oxidizing agent, carbon dioxide can produce carbon monoxide, which can be captured and used as an intermediate in production of other chemical products, such as methanol or formic acid.

The ODH Process

ODH of alkanes includes contacting a mixture of one or more alkanes and oxygen in an ODH reactor with an ODH catalyst under conditions that promote oxidation of the alkanes into their corresponding alkene. Conditions within the reactor are controlled by the operator and include, but are not limited to, parameters such as temperature, pressure, and flow rate. Conditions will vary and can be optimized for a particular alkane, or for a specific catalyst, or whether an inert diluent is used in the mixing of the reactants.

Use of an ODH reactor for performing an ODH process consistent with the disclosure falls within the knowledge of the person skilled in the art. For best results, the oxidative dehydrogenation of one or more alkanes may be conducted at temperatures from 300° C. to 450° C., or from 300° C. to 425° C., or from 330° C. to 400° C., at pressures from 0.5 to 100 psi (3.447 to 689.47 kPa), or from 15 to 50 psi (103.4 to 344.73 kPa), and the residence time of the one or more alkanes in the reactor may be from 0.002 to 30 seconds, or from 1 to 10 seconds.

In some embodiments, the process has a selectivity for the corresponding alkene (ethylene in the case of ethane ODH) of greater than 95%, or for example, greater than 98%. The gas hourly space velocity (GHSV) can be from 500 to 30000 $h^{-1}$, or greater than 1000 $h^{-1}$. In some embodiments, the space-time yield of corresponding alkene (productivity) in g/hour per kg of the catalyst can be at least 900 or above, or greater than 1500, or greater than 3000, or greater than 3500, at 350 to 400° C. In some embodiments, the productivity of the catalyst will increase with increasing temperature until the selectivity is decreased.

ODH Catalyst

Any of the ODH catalysts known in the art are suitable for use in the methods disclosed herein. Non-limiting examples of suitable oxidative dehydrogenation catalyst include those containing one or more mixed metal oxides selected from:

i) catalysts of the formula:

$$MO_aV_bTe_cNb_dPd_eO_f$$

where a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to satisfy the valence state of the catalyst;

ii) catalysts of the formula:

$$Ni_gA_hB_iD_jO_f$$

where g is a number from 0.1 to 0.9, in many cases from 0.3 to 0.9, in other cases from 0.5 to 0.85, in some instances 0.6 to 0.8; h is a number from 0.04 to 0.9; i is a number from 0 to 0.5; j is a number from 0 to 0.5; and f is a number to satisfy the valence state of the catalyst; A is chosen from Ti, Ta, V, Nb, Hf, W, Y, Zn, Zr, Si and Al or mixtures thereof; B is chosen from La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof; D is chosen from Ca, K, Mg, Li, Na, Sr, Ba, Cs, and Rb and mixtures thereof; and O is oxygen;

iii) catalysts of the formula:

$$MO_aE_kG_lO_f$$

where E is chosen from Ba, Ca, Cr, Mn, Nb, Ta, Ti, Te, V, W and mixtures thereof; chosen from Bi, Ce, Co, Cu, Fe, K, Mg, V, Ni, P, Pb, Sb, Si, Sn, Ti, U, and mixtures thereof; a=1; k is 0 to 2; l=0 to 2, with the proviso that the total value of l for Co, Ni, Fe and mixtures thereof is less than 0.5; and f is a number to satisfy the valence state of the catalyst;

iv) catalysts of the formula:

$$V_mMo_nNb_oTe_pMe_qO_f$$

where Me is chosen from Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to satisfy the valence state of the catalyst;

v) catalysts of the formula:

$$MO_aV_rX_sY_tZ_uM_vO_f$$

where X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to satisfy the valence state of the catalyst;

vi) a mixed metal oxide having the empirical formula:

$$Mo_{6.5-7.0}V_3O_d$$

where d is a number to satisfy the valence of the oxide.

vii) a mixed metal oxide having the empirical formula:

$$Mo_{6.25-7.25}V_3O_d$$

where d is a number to satisfy the valence of the oxide.

When choosing a catalyst, a those skilled in the art can appreciate that catalysts may vary with respective to selectivity and activity. Some embodiments of ODH of ethane in this disclosure use a mixed metal oxide catalysts that can provide high selectivity to ethylene without significant loss in activity. Non-limiting example catalysts are those of the formula:

$$MO_aV_bTe_cNb_dPd_eO_f$$

wherein a, b, c, d, e and f are the relative atomic amounts of the elements Mo, V, Te, Nb, Pd and 0, respectively, and when a=1, b=0.01 to 1.0, c=0.01 to 1.0, d=0.01 to 1.0, 0.00≤e≤0.10 and f is a number to satisfy the valence state of the catalyst and a mixed metal oxide having the empirical formula:

$$Mo_{6.25-7.25}V_3O_d$$

where d is a number to satisfy the valence of the oxide.

In some embodiments, the catalyst may be supported on/agglomerated with a binder. Some binders include acidic, basic or neutral binder slurries of $TiO_2$, $ZrO_2$ $Al_2O_3$, AlO (OH) and mixtures thereof. Another useful binder includes $Nb_2O_5$. The agglomerated catalyst may be extruded in a suitable shape (rings, spheres, saddles etc.) of a size typically used in fixed bed reactors. When the catalyst is extruded, various extrusion aids known in the art can be used. In some cases, the resulting support may have a cumulative surface area of less than 35 m²/g as measured by BET, in some cases, less than 20 m²/g, in other cases, less than 3 m²/g. and a cumulative pore volume from 0.05 to 0.50 cm/g.

ODH Reactor

Any of the known reactor types applicable for the ODH of alkanes may be used with the methods disclosed herein. In some embodiments, the methods may be used with conventional fixed bed reactors. In a typical fixed bed reactor, reactants are introduced into the reactor at one end, flow past an immobilized catalyst, products are formed and leave at the other end of the reactor. Designing a fixed bed reactor suitable for the methods disclosed herein can follow techniques known for reactors of this type. A person skilled in the art would know which features are required with respect to shape and dimensions, inputs for reactants, outputs for products, temperature and pressure control, and means for immobilizing the catalyst.

In some embodiments, the use of inert non-catalytic heat dissipative particles can be used within one or more of the ODH reactors. In various embodiments, the heat dissipative particles are present within the bed and include one or more non catalytic inert particulates having a melting point at least 30° C., in some embodiments at least 250° C., in further embodiments at least 500° C. above the temperature upper control limit for the reaction; a particle size in range of 0.5 to 75 mm, in some embodiments 0.5 to 15, in further embodiments in range of 0.5 to 8, in further embodiments in the range of 0.5 to 5 mm; and a thermal conductivity of greater than 30 W/mK (watts/meter Kelvin) within the reaction temperature control limits. In some embodiments the particulates are metal alloys and compounds having a thermal conductivity of greater than 50 W/mK (watts/meter Kelvin) within the reaction temperature control limits. Non-limiting examples of suitable metals that can be used in these embodiments include, but are not limited to, silver, copper, gold, aluminum, steel, stainless steel, molybdenum, and tungsten.

The heat dissipative particles can have a particle size of from about 1 mm to about 15 mm. In some embodiments, the particle size can be from about 1 mm to about 8 mm. The heat dissipative particles can be added to the fixed bed in an amount from 5 to 95 wt. %, in some embodiments from 30 to 70 wt. %, in other embodiments from 45 to 60 wt. % based on the entire weight of the fixed bed. The particles are employed to potentially improve cooling homogeneity and reduction of hot spots in the fixed bed by transferring heat directly to the walls of the reactor.

Additional embodiments include the use of a fluidized bed reactor, where the catalyst bed can be supported by a porous structure, or a distributor plate, located near a bottom end of the reactor and reactants flow through at a velocity sufficient to fluidize the bed (e.g. the catalyst rises and begins to swirl around in a fluidized manner). The reactants are converted to products upon contact with the fluidized catalyst and the reactants are subsequently removed from the upper end of the reactor. Design considerations those skilled in the art can modify and optimize include, but are not limited to, the shape of the reactor, the shape and size of the distributor plate, the input temperature, the output temperature, and reactor temperature and pressure control.

Embodiments of the disclosure include using a combination of both fixed bed and fluidized bed reactors, each with the same or different ODH catalyst. The multiple reactors can be arrayed in series or in parallel configuration, the design of which falls within the knowledge of the worker skilled in the art.

Oxygen/Alkane Mixture

Safety of the ODH process is a primary concern. For that reason, in many embodiments, mixtures of one or more alkanes with oxygen should be employed using ratios that fall outside of the flammability envelope of the one or more alkanes and oxygen. In some embodiments, the ratio of alkanes to oxygen may fall outside the upper flammability envelope. In these embodiments, the percentage of oxygen in the mixture can be less than 30 wt. %, in some cases less than 25 wt. %, or in other cases less than 20 wt. %.

In embodiments with higher oxygen percentages, alkane percentages can be adjusted to keep the mixture outside of the flammability envelope. While a person skilled in the art would be able to determine an appropriate ratio level, in many cases the percentage of alkane is less than about 40 wt. %. As a non-limiting example, where the mixture of gases prior to ODH includes 20% oxygen and 40% alkane, the balance can be made up with an inert diluent. Non-limiting examples of useful inert diluents in this embodiment include, but are not limited to, one or more of nitrogen, carbon dioxide, and steam. In some embodiments, the inert diluent should exist in the gaseous state at the conditions within the reactor and should not increase the flammability of the hydrocarbon added to the reactor, characteristics that a skilled worker would understand when deciding on which inert diluent to employ. The inert diluent can be added to either of the alkane containing gas or the oxygen containing gas prior to entering the ODH reactor or may be added directly into the ODH reactor.

In some embodiments, mixtures that fall within the flammability envelope may be employed, as a non-limiting example, in instances where the mixture exists in conditions that prevent propagation of an explosive event. In these non-limiting examples, the flammable mixture is created within a medium where ignition is immediately quenched. As a further non-limiting example, a user may design a reactor where oxygen and the one or more alkanes are mixed at a point where they are surrounded by a flame arresting material. Any ignition would be quenched by the surrounding material. Flame arresting materials include, but are not limited to, metallic or ceramic components, such as stainless steel walls or ceramic supports. In some embodiments, oxygen and alkanes can be mixed at a low temperature, where an ignition event would not lead to an explosion, then introduced into the reactor before increasing the temperature. The flammable conditions do not exist until the mixture is surrounded by the flame arrestor material inside of the reactor.

Carbon Monoxide Output

Carbon monoxide can be produced in the ODH reaction as a by-product of oxidation of the one or more alkanes. The carbon monoxide output is a function of the amount of carbon monoxide produced in the oxidative process.

Measuring the amount of carbon monoxide coming off the ODH reactor can be done using any means known in the art. For example, one or more detectors such as GC, IR, or Rahman detectors, are situated immediately downstream of the reactor to measure the carbon monoxide output. While not required, the output of other components may also be measured. These include but are not limited to the amounts of ethylene, unreacted ethane, carbon dioxide and oxygen, and by-products such as acetic acid.

Carbon monoxide output can be stated using any metric commonly used in the art. For example, the carbon monoxide output can be described in terms of mass flow rate (g/min) or volumetric flow rate (cm³/min). In some embodiments, normalized selectivity can be used to assess the degree to which carbon monoxide is produced or consumed. In that instance the net mass flow rate of CO—the difference between the mass flow rate of CO leaving the ODH reactor—is normalized to the conversion of ethane, in essence describing what fraction of ethane is converted into carbon monoxide as opposed to ethylene, or other by-products such as acetic acid.

Many industrial processes, in addition to ODH, produce carbon monoxide which must be captured or flared where it contributes to the emission of greenhouse gases. Using the carbon monoxide mitigation steps disclosed herein converts most, if not all, carbon monoxide resulting from the ODH process to carbon dioxide. An advantage then is the ability to reduce or eliminate the amount of carbon monoxide produced in the ODH process in combination with other processes, such as thermal cracking.

Acetylene Output

Acetylene can be produced in the ODH reaction as a by-product of oxidation of the one or more alkanes. The acetylene output is a function of the amount of acetylene produced in the oxidative process.

Measuring the amount of acetylene coming off the ODH reactor can be done using any means known in the art. For example, one or more detectors such as GC, IR, or Rahman detectors, are situated immediately downstream of the reactor to measure the acetylene output. While not required, the output of other components may also be measured. These include but are not limited to the amounts of ethylene, unreacted ethane, carbon monoxide, carbon dioxide and oxygen, and by-products such as acetic acid.

Acetylene output can be stated using any metric commonly used in the art. For example, the acetylene output can be described in terms of mass flow rate (g/min), volumetric flow rate (cm³/min) or volumetric parts per million (vppm). In some embodiments, normalized selectivity can be used to assess the degree to which acetylene is produced or consumed. In that instance the net mass flow rate of acetylene—the difference between the mass flow rate of acetylene leaving the ODH reactor—is normalized to the conversion of ethane, in essence describing what fraction of ethane is converted into acetylene as opposed to ethylene, or other by-products such as acetic acid.

Using the acetylene mitigation steps disclosed herein reacts most, if not all, acetylene resulting from the ODH process. An advantage then is the ability to reduce or eliminate the amount of acetylene produced in the ODH process in combination with other processes, such as thermal cracking and eliminate downstream unit operations in an ODH-type process.

Addition of Steam

The amount of steam added to the ODH process affects the degree to which carbon dioxide acts as an oxidizing agent. In some embodiments steam may be added directly to the ODH reactor, or steam may be added to the individual reactant components—the lower alkane, oxygen, or inert diluent—or combinations thereof, and subsequently introduced into the ODH reactor along with one or more of the reactant components. Alternatively, steam may be added indirectly as water mixed with either the lower alkane, oxygen or inert diluent, or a combination thereof, with the resulting mixture being preheated before entering the reactor. When adding steam indirectly as water the preheating process should increase the temperature so that the water is entirely converted to steam before entering the reactor.

Increasing the amount of steam added to a reactor increases the degree to which carbon dioxide acts as an oxidizing agent. Decreasing the amount of steam added to the reactor decreases the degree to which carbon dioxide acts as an oxidizing agent. In some embodiments a user monitors the carbon dioxide output and compares it to a predetermined target carbon dioxide output. If the carbon dioxide output is above the target a user can then increase the amount of steam added to the ODH process. If the carbon dioxide output is below the target a user can decrease the amount of steam added to the ODH process, provided steam has been added. Setting a target carbon dioxide output level is dependent on the requirements for the user. In some embodiments increasing the steam added will have the added effect of increasing the amount of acetic acid and other by-products produced in the process. A user that is ill equipped to separate out larger amounts of acetic acid from the output of the ODH may instead reduce steam levels to a minimum, while a user that desires a process that consumes carbon dioxide may choose to maximize the amount of steam that can be added. The amount of steam added to the one or more ODH reactors can be up to about 40 wt. %, in some cases up to about 35 wt. %, in other cases up to about 30 wt. %, and in some instances up to about 25 wt. %.

In some embodiments when using two or more ODH reactors a user may choose to control carbon dioxide output in only one, or less than the whole complement of reactors. For example, a user may opt to maximize carbon dioxide output of an upstream reactor so that the higher level of carbon dioxide can be part of the inert diluent for the subsequent reactor. In that instance, maximizing carbon dioxide output upstream minimizes the amount of inert diluent that would need to be added to the stream prior to the next reactor.

There is no requirement for adding steam to an ODH process, as it is one of many alternatives for the inert diluent. For processes where no steam is added, the carbon dioxide output is maximized under the conditions used with respect to ethane, oxygen and inert diluent inputs. Decreasing the carbon dioxide output is then a matter of adding steam to the reaction until carbon dioxide output drops to the desired level. In embodiments where oxidative dehydrogenation conditions do not include addition of steam, and the carbon dioxide output is higher than the desired carbon dioxide target level, steam may be introduced into the reactor while keeping relative amounts of the main reactants and inert diluent—lower alkane, oxygen and inert diluent—added to the reactor constant, and monitoring the carbon dioxide output, increasing the amount of steam until carbon dioxide decreases to the target level.

In some embodiments, a carbon dioxide neutral process can be achieved by increasing steam added so that any carbon dioxide produced in the oxidative dehydrogenation process can then be used as an oxidizing agent such that there is no net production of carbon dioxide. Conversely, if a user desires net positive carbon dioxide output then the amount of steam added to the process can be reduced or eliminated to maximize carbon dioxide production. As the carbon dioxide levels increase there is potential to reduce oxygen consumption, as carbon dioxide is competing as an oxidizing agent. The skilled person would understand that using steam to increase the degree to which carbon dioxide acts as an oxidizing agent can impact oxygen consumption. The implication is that a user can optimize reaction conditions with lower oxygen contributions, which may assist in keeping mixtures outside of flammability limits.

In embodiments of the invention, the stream exiting the one or more ODH reactors can be treated to remove or separate water and water soluble hydrocarbons from the stream exiting the one or more ODH reactors. In particular embodiments, this stream is fed to a CO Oxidation reactor.

Acetic Acid Removal

Prior to being fed to the CO Oxidation Reactor, the stream exiting the one or more ODH reactors is directed to quench tower or acetic acid scrubber, which facilitates removal of oxygenates, such as acetic acid, and water via a bottom outlet. A stream containing unconverted lower alkane (such as ethane), corresponding alkene (such as ethylene), unreacted oxygen, carbon dioxide, carbon monoxide, optionally acetylene and inert diluent, are allowed to exit the scrubber and are fed to the CO Oxidation Reactor.

The oxygenates removed via the quench tower or acetic acid scrubber can include carboxylic acids (for example acetic acid), aldehydes (for example acetaldehyde) and ketones (for example acetone). The amount of oxygenate compounds remaining in the stream exiting the scrubber and fed to the CO Oxidation Reactor will often be zero, i.e, below the detection limit for analytical test methods typically used to detect such compounds. When oxygenates can be detected they can be present at a level of up to about 1 per million by volume (ppmv), in some cases up to about 5 ppmv, in other cases less than about 10 ppmv, in some instances up to about 50 ppmv and in other instances up to about 100 ppmv and can be present up to about 2 vol. %, in some cases up to about 1 vol. %, and in other cases up to about 1,000 ppmv. The amount of oxygenates or acetic acid in the stream exiting the scrubber and fed to the CO Oxidation Reactor can be any value, or range between any of the values recited above.

The CO Oxidation Reactor

In many embodiments, the ODH reactor (or reactors) can provide a stream containing at least a small amount of oxygen remaining as reactor effluent. In embodiments of the disclosure, the oxygen can provide a benefit to the ODH reactor product gas. In some embodiments, when the ODH catalyst is exposed to an oxygen free reducing environment at elevated temperature, it may become permanently degraded. In other embodiments, if the level of oxygen in the product gas from the ODH reactor contains less than about 1 ppm of oxygen, most, if not all, of the one or more alkanes are converted to one or more alkenes in the inlet portion of the reactor and a large portion of the reactor catalyst bed is not utilized.

In other embodiments, oxygen in the ODH reactor product gas causes serious safety and operational issues in the downstream equipment, as a non-limiting example, at the first compression stage of an ODH process. This process safety consideration presents a need to remove oxygen to a very low or non-detectable level before the product gas is compressed.

One method used to reduce/eliminate oxygen in the ODH product gas focuses on catalytically combusting a small portion of the ODH product gas to the complete consumption of any residual oxygen. This approach is viable, however, in many cases it is undesirable, because it increases the overall oxygen consumption in the ODH process and, in the non-limiting example of the alkane being ethane, reduces overall process selectivity toward ethylene.

This disclosure describes a process where the ODH reaction can proceed with partial consumption of $CO_2$ ($CO_2$ can act as an oxidizing agent, and be converted to CO), reducing overall oxygen consumption in the process by providing a portion of the required oxygen from $CO_2$. In many embodiments, more oxygen passes through the catalyst bed unconverted when $CO_2$ is provided and acts as an oxidizing agent.

Oxidation of Carbon Monoxide

In the process of this disclosure, the ODH reactor product stream is fed to the CO Oxidation reactor, which contains a catalyst that includes one or more selected from a group 11 metal, a group 4 metal, a group 7, a group 9 metal, a lanthanide metal, and an actinide metal and/or their corresponding metal oxides capable of converting at least a portion of the carbon monoxide to carbon dioxide. The carbon dioxide can be recycled to the ODH reactor to act as an oxidizing agent as described above.

In embodiments of the disclosure, the group 11 metal can be selected from copper, silver, gold and combinations thereof. In certain embodiments of the disclosure, the group 11 metal is silver or copper.

In embodiments of the disclosure, the group 4 metal can be selected from titanium, zirconium, hafnium, rutherfordium and combinations thereof. In certain embodiments of the disclosure, the group 4 metal is zirconium.

In embodiments of the disclosure, the group 7 metal can be selected from manganese, technetium, rhenium, bohrium and combinations thereof. In certain embodiments of the disclosure, the group 7 metal is manganese.

In embodiments of the disclosure, the group 9 metal can be selected from cobalt, rhodium, iridium, meiternium and combinations thereof. In certain embodiments of the disclosure, the group 9 metal is cobalt.

In embodiments of the disclosure, the lanthanide metal can be selected from La, Ce, Pr, Nd, Pm, Sm, Eu, Gd, Tb, Dy, ho, Er, Tm, Yb and combinations thereof. In certain embodiments of the disclosure, the lanthanide metal is Cerium.

In embodiments of the disclosure, the actinide metal can be selected from Ac, Th, Ps, U, Np, Pu, Am, Cm, Bk, Cf, Es, Fm, Md, No and combinations thereof. In certain embodiments of the disclosure, the actinide metal is thorium.

In embodiments of the disclosure, the CO Oxidation reactor catalyst, in some cases a group 11 metal, is used in conjunction with a promoter. In many embodiments, the promoter is selected from one or more of the lanthanide and actinide metals (as defined above) and their corresponding metal oxides. In certain embodiments, the promoter is selected from one or more of the lanthanide metals and their corresponding metal oxides. In particular embodiments the promoter includes cerium and its corresponding metal oxides.

In embodiments of the disclosure, the CO Oxidation reactor catalyst, in some cases a group 11 metal, and optional promotor are provided on a support. The support is typically an inert solid with a high surface area, to which the CO Oxidation reactor catalyst and optional promotor can be affixed. In many embodiments, the support includes Si, Ge, Sn, their corresponding oxides and combinations thereof.

In embodiments of the disclosure, non-limiting examples of suitable CO Oxidation reactor catalysts with optional promotors and supports include $Ag/SiO_2$, $AgCeO_2/SiO_2$, $AgZrO_2/SiO_2$, $AgCo_3O_4/SiO_2$, $Cu/SiO_2$, $CuCeO_2/SiO_2$, $CuZrO_2/SiO_2$, $CuCo_3O_4/SiO_2$ and combinations thereof.

In other embodiments of the disclosure, non-limiting examples of suitable CO Oxidation reactor catalysts with optional promotors and supports include $AgCeO_2/SiO_2$, $AgZrO_2/SiO_2$ and combinations thereof.

In specific embodiments of the disclosure, the CO Oxidation reactor catalyst includes silver, the optional promoter includes cerium and the support includes $SiO_2$.

In specific embodiments of the disclosure, the CO Oxidation reactor catalyst includes copper, the optional promoter includes cerium and the support includes $SiO_2$.

In specific embodiments of the disclosure, when oxidation of carbon monoxide is preferentially desired, the CO Oxidation reactor catalyst includes manganese, the optional promoter includes cerium and the support includes $SiO_2$.

In embodiments of the disclosure, the group 11 metal with optional promoter and optional support can be used in a process where 1) some oxygen is in the stream leaving the ODH reactor: 2) the temperature in the stream is decreased; 3) the cooled stream is fed to an acetic acid scrubber; 4) the stream from the acetic acid scrubber is fed to reactor 2 as described above, where most or all of the residual $O_2$ is consumed and CO is converted to $CO_2$; and 5) optionally, the $CO_2$ is recycled back to the ODH reactor.

In embodiments of the disclosure, the amount of oxygen in the stream leaving the ODH reactor in 1) can be at least about 80 ppm, in some cases at least about 100 ppm, in other cases at least about 150 ppm and in some instances at least about 200 ppm and can be up to about 5 wt. %, in some cases up to about 4 wt. %, in other cases up to about 3 wt. %, in some instances up to about 2 wt. %, in other instances up to about 1 wt. %, and in particular situations up to about 500 ppm. The amount of oxygen in the stream leaving the ODH reactor in 1) can be any of the values or range between any of the values recited above.

In embodiments of the disclosure, when there is oxygen in the stream leaving the CO Oxidation reactor (in some instances the amount of oxygen will be undetectable or zero ppm), the amount of oxygen in the stream leaving the CO Oxidation reactor can be at least about 1 ppm, in some cases at least about 2 ppm, in other cases at least about 3 ppm and in some instances at least about 5 ppm and can be up to about 1 wt. %, in some cases up to about 0.9 wt. %, in other cases up to about 0.8 wt. %, in some instances up to about 0.7 wt. %, in other instances up to about 0.6 wt. %, and in particular situations up to about 0.5 wt. %. The amount of oxygen in the stream leaving the CO Oxidation reactor can be any of the values or range between any of the values recited above.

In embodiments of the disclosure, the amount of carbon monoxide in the stream leaving the ODH reactor in 1) can be at least about 100 ppm, in some cases at least about 200 ppm, in other cases at least about 300 ppm and in some instances at least about 400 ppm and can be up to about 10 wt. %, in some cases up to about 9 wt. %, in other cases up to about 8 wt. %, in some instances up to about 7 wt. %, in other instances up to about 6 wt. %, and in particular situations up to about 5 wt. %. The amount of carbon monoxide in the stream leaving the ODH reactor in 1) can be any of the values or range between any of the values recited above.

In embodiments of the disclosure, when there is carbon monoxide in the stream leaving the CO Oxidation reactor (in some instances the amount of carbon monoxide will be undetectable or zero ppm), the amount of carbon monoxide in the stream leaving the CO Oxidation reactor can be at least about 1 ppm, in some cases at least about 2 ppm, in other cases at least about 3 ppm and in some instances at least about 5 ppm and can be up to about 8 wt. %, in some cases up to about 7 wt. %, in other cases up to about 6 wt. %, in some instances up to about 5 wt. %, in other instances up to about 4 wt. %, and in particular situations up to about 3 wt. %. The amount of carbon monoxide in the stream leaving the CO Oxidation reactor can be any of the values or range between any of the values recited above.

In embodiments of the disclosure, temperature in the CO Oxidation reactor can be at least about 40, in some cases at least about 45, in other cases at least about 50 and in some instances at least about 55° C. and can be up to about 200, in some instances up to about 150, in other instances up to about 120, in some circumstances up to about 90, in some cases up to about 85, in other cases up to about 80, in some instances up to about 75 and in other instances up to about 70° C. The temperature of the CO Oxidation reactor can be any temperature value or range between any of the temperature values, including a temperature gradient within the CO Oxidation reactor, recited above.

Acetylene Elimination

In the process of this disclosure, the ODH reactor product stream is fed to the CO Oxidation reactor, which contains a catalyst that includes one or more selected from a group 11 metal, a group 4 metal, a group 9 metal, a lanthanide metal, and an actinide metal and/or their corresponding metal oxides capable of reacting at least a portion of the acetylene.

In embodiments of the disclosure, the group 11 metal can be selected from copper, silver, gold and combinations thereof. In certain embodiments of the disclosure, the group 11 metal is silver.

In embodiments of the disclosure, the group 4 metal can be selected from titanium, zirconium, hafnium, rutherfordium and combinations thereof. In certain embodiments of the disclosure, the group 4 metal is zirconium.

In embodiments of the disclosure, the group 9 metal can be selected from cobalt, rhodium, iridium, meiternium and combinations thereof. In certain embodiments of the disclosure, the group 9 metal is cobalt.

In embodiments of the disclosure, the lanthanide metal can be selected from La, Ce, Pr, Nd, Pm, Sm, Eu, Gd, Tb, Dy, ho, Er, Tm, Yb and combinations thereof. In certain embodiments of the disclosure, the lanthanide metal is Cerium.

In embodiments of the disclosure, the actinide metal can be selected from Ac, Th, Ps, U, Np, Pu, Am, Cm, Bk, Cf, Es, Fm, Md, No and combinations thereof. In certain embodiments of the disclosure, the actinide metal is thorium.

In embodiments of the disclosure, the CO Oxidation reactor catalyst, in some cases a group 11 metal, is used in conjunction with a promoter. In many embodiments, the promoter is selected from one or more of the lanthanide and actinide metals (as defined above) and their corresponding metal oxides. In certain embodiments, the promoter is selected from one or more of the lanthanide metals and their corresponding metal oxides. In particular embodiments the promoter includes cerium and its corresponding metal oxides.

In embodiments of the disclosure, the CO Oxidation reactor catalyst, in some cases a group 11 metal, and optional promotor are provided on a support. The support is typically an inert solid with a high surface area, to which the CO Oxidation reactor catalyst and optional promotor can be affixed. In many embodiments, the support includes Si, Ge, Sn, their corresponding oxides and combinations thereof.

In embodiments of the disclosure, non-limiting examples of suitable CO Oxidation reactor catalysts with optional promotors and supports include $Ag/SiO_2$, $AgCeO_2/SiO_2$, $AgZrO_2/SiO_2$, $AgCo_3O_4/SiO_2$, $Cu/SiO_2$, $CuCeO_2/SiO_2$, $CuZrO_2/SiO_2$, $CuCo_3O_4/SiO_2$ and combinations thereof.

In other embodiments of the disclosure, non-limiting examples of suitable CO Oxidation reactor catalysts with optional promotors and supports include $AgCeO_2/SiO_2$, $AgZrO_2/SiO_2$ and combinations thereof.

In specific embodiments of the disclosure, the CO Oxidation reactor catalyst includes silver, the optional promoter includes cerium and the support includes $SiO_2$.

In specific embodiments of the disclosure, the CO Oxidation reactor catalyst includes copper, the optional promoter includes cerium and the support includes $SiO_2$.

In embodiments of the disclosure, the group 11 metal with optional promoter and optional support can be used in a process where 1) some acetylene is in the stream leaving the ODH reactor; 2) the temperature in the stream is decreased; 3) the cooled stream is fed to an acetic acid scrubber; 4) the stream from the acetic acid scrubber is fed to reactor 2 as described above, where most or all of the acetylene is consumed and CO is oxidized to $CO_2$; and 5) optionally, the $CO_2$ is recycled back to the ODH reactor.

In embodiments of the disclosure, when there is acetylene in the stream leaving the ODH reactor (in some instances the amount of acetylene will be undetectable or zero vppm), the amount of acetylene in the stream leaving the ODH reactor in 1) can be at least about 1 vppm, in some cases at least about 2 vppm, in other cases at least about 5 vppm and in some instances at least about 10 vppm and can be up to about 1000 vppm, in some cases up to about 750 vppm, in other cases up to about 500 vppm, in some instances up to about 400 vppm, in other instances up to about 300 vppm, and in particular situations up to about 300 vppm. The amount of acetylene in the stream leaving the ODH reactor in 1) can be any of the values or range between any of the values recited above.

In embodiments of the disclosure, the amount of acetylene in the stream leaving the CO Oxidation reactor will be less than the amount entering the CO Oxidation reactor and, in many instances, the stream exiting the CO Oxidation reactor will be substantially free of acetylene.

In embodiments of the disclosure, when there is acetylene in the stream leaving the CO Oxidation reactor (in many instances the amount of acetylene will be undetectable or zero vppm), the amount of acetylene in the stream leaving the CO Oxidation reactor can be at least about 1 vppm, in some cases at least about 2 vppm, in other cases at least about 3 vppm and in some instances at least about 5 vppm and can be up to about 100 vppm, in some cases up to about 50 vppm, in other cases up to about 25 vppm, in some instances up to about 20 vppm, in other instances up to about 15 vppm, and in particular situations up to about 10 vppm. The amount of acetylene in the stream leaving the CO Oxidation reactor can be any of the values or range between any of the values recited above.

In embodiments of the disclosure, temperature in the CO Oxidation reactor can be at least about 40, in some cases at least about 45, in other cases at least about 50 and in some instances at least about 55° C. and can be up to about 200, in some instances up to about 150, in other instances up to about 120, in some circumstances up to about 90, in some cases up to about 85, in other cases up to about 80, in some instances up to about 75 and in other instances up to about 70° C. The temperature of CO Oxidation reactor can be any temperature value or range between any of the temperature values, including a temperature gradient within the CO Oxidation reactor, recited above.

As indicated above, when ethylene from the ODH process described herein is used in a VAM process and the ethylene stream contains carbon monoxide, it can poison the VAM catalyst and minimize or prevent the production of vinyl acetate monomer. When used to produce vinyl acetate monomer as described herein, one or more CO Oxidation reactors can be employed.

As indicated herein, one role of the one or more CO Oxidation reactors is to oxidize at least a portion of, in some cases substantially all, of the carbon monoxide to carbon dioxide in the product stream from the one or more ODH reactors. In this context, oxidizing substantially all of the carbon monoxide to carbon dioxide means that the stream exiting any of the CO Oxidation reactors contains very low amounts, undetectable amounts or no carbon monoxide. When the amount of oxygen in the stream entering the CO Oxidation reactor is insufficient to oxidize the carbon monoxide in the entering stream, the CO Oxidation reactor can be equipped with a supplementary oxygen feed, which is adapted to provide an oxygen containing gas sufficient to oxidize all of the carbon monoxide to carbon dioxide.

In embodiments of the disclosure, monitoring equipment and feed back loops known in the art can be used to adjust the amount of oxygen provided to a CO Oxidation reactor so that the amount of oxygen in the stream entering the CO Oxidation reactor is about equal to the amount required to oxidize the carbon monoxide in entering stream to carbon dioxide.

In particular embodiments, when oxygen is provided to the one or more CO Oxidation reactors, the stream exiting the CO Oxidation reactor can contain no carbon monoxide (undetectable or 0 ppm), in some cases no more than about 10 ppm, in other cases no more than about 20 ppm and in some instances no more than about 30 ppm of carbon monoxide. Additionally, the stream exiting the CO Oxidation reactor can contain up to about 125 ppm, in some cases up to about 100 ppm, in other cases up to about 75 ppm and in some instances up to about 50 ppm of carbon monoxide. The amount of carbon monoxide in the stream exiting the CO Oxidation reactor is low enough to minimize or mitigate any poisoning of the VAM catalyst and can be any of the values or range between any of the values recited above.

In embodiments of the disclosure, the stream from the ODH reactor is cooled to a lower temperature prior to being fed to an acetic acid scrubber (as described below). The temperature of the stream prior to entering the acetic acid scrubber can be at least about 40, in some cases at least about 45, and in other cases at least about 50° C. and can be up to about 90, in some cases up to about 85, in other cases up to about 80, in some instances up to about 75 and in other instances up to about 70° C. The temperature of the ODH reactor product stream fed to an acetic acid scrubber can be cooled to any temperature value or range between any of the temperature values recited above.

In embodiments of the disclosure, the configuration described above can allow for the size of the air separation plant to be reduced, as well as improving the life of the ODH catalyst, by allowing it to be exposed to an oxygen containing environment at all times. In additional embodiments, the configuration described above can improve the reliability and safety of the ODH reactor and downstream equipment.

In embodiments of the disclosure, the net $CO_2$ generation in the process described herein can be optimized to be zero. In these embodiments, the need to flare off any $CO_2$ (with some amount of alkane/alkene) from the $CO_2$-recycle loop as described herein is minimized. In these embodiments, the total process yield of alkane to alkene can be improved.

The VAM Process

In the VAM process, an ethylene containing stream, where substantially all of the carbon monoxide has been oxidized to carbon dioxide, is reacted with acetic acid from the acetic acid scrubber (the VAM Process Stream) to provide vinyl acetate monomer. In many embodiments this includes contacting ethylene and acetic acid with an oxygen-containing gas in the presence of a catalyst to produce a product stream that includes vinyl acetate. The product stream can be separated to recover vinyl acetate monomer from the product stream.

The VAM process stream includes acetic acid and ethylene in a predetermined ratio with water, and may contain ethane, oxygen, nitrogen and the by-products, and carbon dioxide. As indicated above, no or very small amounts (<120 ppm) of carbon monoxide are present. Optionally, an oxygen-containing gas, can be included in the VAM process.

The catalyst active for the production of vinyl acetate which is used in the VAM process contains a metal selected from the group 10 and group 11 metals and combinations thereof.

In embodiments of the disclosure, any suitable catalyst for the VAM process known in the art can be used, particular non-limiting examples include, but are not limited to a shell impregnated catalyst that includes (1) a catalyst support having a particle diameter from about 3 to about 7 mm and a pore volume of about 0.2 to about 1.5 ml per gram; (2) palladium and gold; and (3) from about 3.5 to about 9.5% by weight of potassium acetate wherein the gold to palladium weight ratio in the catalyst is in the range of from about 0.60 to about 1.25; catalysts of this type are described, for example, in EP-A 330 853, GB 1 559 540, U.S. Pat. No. 5,185,308, and WO 99/08791; catalysts as described in EP-A 0 330 853 and containing Pd, K, Mn and Cd as an additional promotor instead of Au; catalysts described in GB 1 559 540 containing (1) a catalyst support having a particle diameter of from about 3 to about 7 mm and a pore volume of from about 0.2 to about 1.5 ml/g, an approximately 10% by weight water suspension of the catalyst support having a pH from about 3 to about 9; (2) a palladium-gold alloy distributed in a surface layer of the catalyst support, the surface layer extending less than about 0.5 mm from the surface of the support, the palladium in the alloy being present in an amount of from about 1.5 to about 5.0 g/l of catalyst, and the gold being present in an amount of from about 0.5 to about 2.25 grams per liter of catalyst; and (3) from about 5 to about 60 g/l of catalyst of alkali metal acetate.

U.S. Pat. No. 5,185,308 describes a shell impregnated catalyst active for the production of vinyl acetate from ethylene, acetic acid and an oxygen containing gas, the catalyst contains: (1) a catalyst support having a particle diameter from about 3 to about 7 mm and a pore volume of from about 0.2 to 1.5 ml/g; (2) palladium and gold distributed in the outermost about 1 mm thick layer of the catalyst support particles; and (3) from about 3.5 to about 9.5% by weight of potassium acetate where the gold to palladium weight ratio in the catalyst is in the range of from about 0.6 to about 1.25.

ODH-VAM Complex

In the following description of the present disclosure for reference to the figures it should be noted that like parts are designated by like reference numbers.

In embodiments of the disclosure, the chemical complex of the present disclosure, shown in one embodiment schematically in FIG. 1, includes, in cooperative arrangement, an ODH reactor 10, a quench tower or acetic acid scrubber 20, a first CO Oxidation reactor 30 (as described herein), a vinyl acetate monomer (VAM) reactor 40, a VAM separation unit 50 and an inert removal unit 70. Although first CO Oxidation reactor 30 is shown directly after quench tower or acetic acid scrubber 20, it can be placed further downstream. In many cases, the process configuration can be more energy efficient if first CO Oxidation reactor 30 is placed after the input stream has been compressed.

ODH reactor 10 includes an ODH catalyst capable of catalyzing, in the presence of oxygen which may be introduced via oxygen line 80, the oxidative dehydrogenation of alkanes introduced via alkane line 90. The ODH reaction may also occur in the presence of an inert diluent, such as carbon dioxide, nitrogen, or steam, that is added to ensure the mixture of oxygen and hydrocarbon are outside of flammability limits. Determination of whether a mixture is outside of the flammability limits, for the prescribed temperature and pressure, is within the knowledge of the skilled worker. An ODH reaction that occurs within ODH reactor 10 may also produce, depending on the catalyst and the prevailing conditions within ODH reactor 10, a variety of other products which may include carbon dioxide, carbon monoxide, oxygenates, and water. These products leave ODH reactor 10, along with unreacted alkane, corresponding alkene, residual oxygen, carbon monoxide and inert diluent, if added, via ODH reactor product line 100.

ODH reactor product line 100 is directed to quench tower or acetic acid scrubber 20 which quenches the products from product line 100, and facilitates removal of acetic acid and water via quench tower bottom outlet 110. Unconverted lower alkane, corresponding alkene, unreacted oxygen, carbon dioxide, carbon monoxide, and inert diluent added to quench tower 20 exit through quench tower overhead line 120 and a portion are directed into first oxidation reactor 30 via first oxidation line 130.

First oxidation reactor 30 contains a group 11 metal with optional promoter and optional support as described above. First oxidation reactor 30 optionally includes first oxygen line 140 which can be used to provide an oxygen containing gas to first oxidation reactor 30. In first oxidation reactor 30, unreacted oxygen is reacted with carbon monoxide to form carbon dioxide and/or, reacts acetylene to reduce or eliminate it. In first oxidation reactor 30, most or all of the unreacted oxygen is consumed. The remaining unconverted lower alkane, corresponding alkene, unreacted oxygen (if present), all or part of the carbon dioxide, carbon monoxide (if present), and inert diluent are directed to first ethylene product line 150 and combined with the acetic acid and water via quench tower bottom outlet 110 and conveyed to the VAM process.

In the VAM process, the contents of quench tower bottom outlet 110 often contains an acetic acid-water mixture with optional traces of ethane/ethylene/CO/CO2. This can be mixed into effluent stream 150, which often contains ethane/ethylene/CO/CO2/O2 with an optional trace of acetic acid and water and can be fed to VAM reactor 40, where acetic acid and ethylene are combined in the presence of a catalyst active for the production of vinyl acetate. VAM reactor 40 optionally includes VAM oxygen line 145 which can be used to provide an oxygen containing gas to VAM reactor 40 as described herein. Depending on the scale of the process, VAM reactor 40 may include either a single reactor or several reactors in parallel or in series. A VAM product stream 300 that includes vinyl acetate, water, optionally ethane, gaseous by-products and unreacted acetic acid and ethylene is withdrawn from VAM reactor 40 and is fed to VAM separation unit 50 where a VAM gaseous stream 330, which can include ethylene, and optionally ethane together with inert compounds, carbon monoxide and carbon dioxide is separated from water and acetic acid, and which can alternatively be withdrawn overhead via first recycle line 310 and can be recycled to and mixed with the contents of quench tower bottom outlet 110 and provided to VAM reactor 40 as described above.

VAM liquid stream 320, which includes vinyl acetate, water, optionally unreacted acetic acid and optionally high boiling by-products of the process are withdrawn from the base of VAM separation unit 50 and vinyl acetate is isolated in state of the art equipment not shown. As a non-limiting example, the contents of VAM liquid stream 320 can be fed to a distillation column where vinyl acetate and water are removed as an azeotrope and acetic acid and the optional high boiling by-products are removed as a bleed from the base of the distillation column. The water in the overhead stream from the distillation column can be separated from the vinyl acetate in a decanter and a vinyl acetate product stream removed from decanter is purified by conventional means known in the art.

VAM gaseous stream 330 is directed to inert removal unit 70, where carbon dioxide and other inert compounds are separated and directed to outlet stream 340 and ethylene and optionally ethane and remaining carbon monoxide are directed to ethylene containing stream 350 and combined into quench tower overhead line 120.

Figure 2:
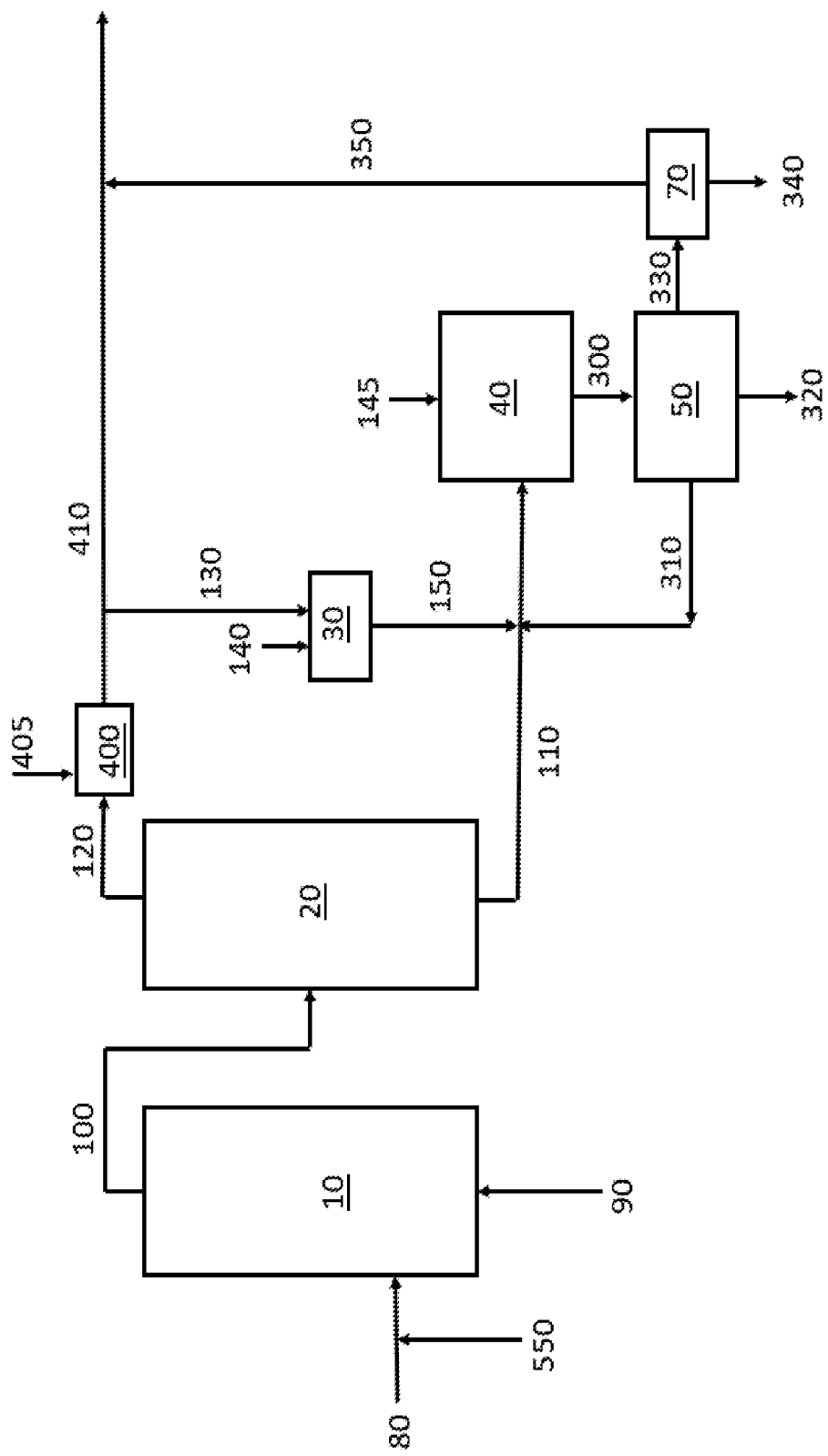
FIG. 2 is a graphic depiction of portions of a chemical complex according to some embodiments of the disclosure.

In embodiments of the disclosure, the chemical complex of the present disclosure, shown in another embodiment schematically in FIG. 2, includes, in cooperative arrangement, an ODH reactor 10, a quench tower or acetic acid scrubber 20, a first CO oxidation reactor 30 (as described herein), a vinyl acetate monomer (VAM) reactor 40, a VAM separation unit 50 and an inert removal unit 70.

As indicated above, with reference to FIG. 1, in the ODH process configuration depicted in FIG. 2, although first CO oxidation reactor 30 is shown directly after quench tower or acetic acid scrubber 20, it can be placed further downstream. In many cases, the process configuration can be more energy efficient if first CO oxidation reactor 30 is placed after the input stream has been compressed.

ODH reactor 10 includes an ODH catalyst capable of catalyzing, in the presence of oxygen which may be introduced via oxygen line 80, the oxidative dehydrogenation of alkanes introduced via alkane line 90. The ODH reaction may also occur in the presence of an inert diluent, such as carbon dioxide, nitrogen, or steam, that is added to ensure the mixture of oxygen and hydrocarbon are outside of flammability limits. Determination of whether a mixture is outside of the flammability limits, for the prescribed temperature and pressure, is within the knowledge of the skilled worker. An ODH reaction that occurs within ODH reactor 10 may also produce, depending on the catalyst and the prevailing conditions within ODH reactor 10, a variety of other products which may include carbon dioxide, carbon monoxide, oxygenates, and water. These products leave ODH reactor 10, along with unreacted alkane, corresponding alkene, residual oxygen, carbon monoxide and inert diluent, if added, via ODH reactor product line 100.

ODH reactor product line 100 is directed to quench tower or acetic acid scrubber 20 which quenches the products from product line 100, and facilitates removal of acetic acid and water via quench tower bottom outlet 110. Unconverted lower alkane, corresponding alkene, unreacted oxygen, carbon dioxide, carbon monoxide, and inert diluent added to quench tower 20 exit through quench tower overhead line 120.

Quench tower overhead line 120 is fed to primary oxidation reactor 400, which contains a group 11 metal with optional promoter and optional support as described above. In primary oxidation reactor 400, unreacted oxygen is reacted with carbon monoxide to form carbon dioxide. In primary oxidation reactor 400, most or all of the unreacted oxygen is consumed. Primary oxidation reactor 400 optionally includes first oxygen line 405 which can be used to provide an oxygen containing gas to primary oxidation reactor 400. The remaining unconverted lower alkane, corresponding alkene, unreacted oxygen (if present), all or part of the carbon dioxide, carbon monoxide (if present), and inert diluent are directed to primary ethylene product line 410.

A portion of the contents of primary ethylene product line 410 are directed to first oxidation reactor 30 via first oxidation line 130. First oxidation reactor 30 operates similar to primary oxidation reactor 400 and reacts any remaining oxygen with carbon monoxide to form carbon dioxide and/or reduces or eliminates acetylene. The remaining unconverted lower alkane, corresponding alkene, unreacted oxygen (if present), all or part of the carbon dioxide, carbon monoxide (if present), and inert diluent are directed to first ethylene product line 150 and combined with the acetic acid and water via quench tower bottom outlet 110 and conveyed to the VAM process.

In the VAM process, the contents of quench tower bottom outlet 110 often contains an acetic acid-water mixture with optional traces of ethane/ethylene/CO/$CO_2$. This can be mixed into effluent stream 150, which often contains ethane/ethylene/CO/$CO_2$/$O_2$ with an optional trace of acetic acid and water and can be fed to VAM reactor 40, where acetic acid and ethylene are combined in the presence of a catalyst active for the production of vinyl acetate. VAM reactor 40 optionally includes VAM oxygen line 145 which can be used to provide an oxygen containing gas to VAM reactor 40 as described herein. Depending on the scale of the process, VAM reactor 40 may include either a single reactor or several reactors in parallel or in series. A VAM product stream 300 that includes vinyl acetate, water, optionally ethane, gaseous by-products and unreacted acetic acid and ethylene is withdrawn from VAM reactor 40 and is fed to VAM separation unit 50 where a VAM gaseous stream 330, which can include ethylene, and optionally ethane together with inert compounds, carbon monoxide and carbon dioxide is separated from water and acetic acid, and which can alternatively be withdrawn overhead via first recycle line 310 and can be recycled to and mixed with the contents of quench tower bottom outlet 110 and provided to VAM reactor 40 as described above.

VAM liquid stream 320, which includes vinyl acetate, water, optionally unreacted acetic acid and optionally high boiling by-products of the process are withdrawn from the base of VAM separation unit 50 and vinyl acetate is isolated in state of the art equipment not shown. As a non-limiting example, the contents of VAM liquid stream 320 can be fed to a distillation column where vinyl acetate and water are removed as an azeotrope and acetic acid and the optional high boiling by-products are removed as a bleed from the base of the distillation column. The water in the overhead stream from the distillation column can be separated from the vinyl acetate in a decanter and a vinyl acetate product stream removed from decanter is purified by conventional means known in the art.

VAM gaseous stream 330 is directed to inert removal unit 70, where carbon dioxide and other inert compounds are separated and directed to outlet stream 340 and ethylene and optionally ethane and remaining carbon monoxide are directed to ethylene containing stream 350 and combined into primary ethylene product line 410.

Figure 3:
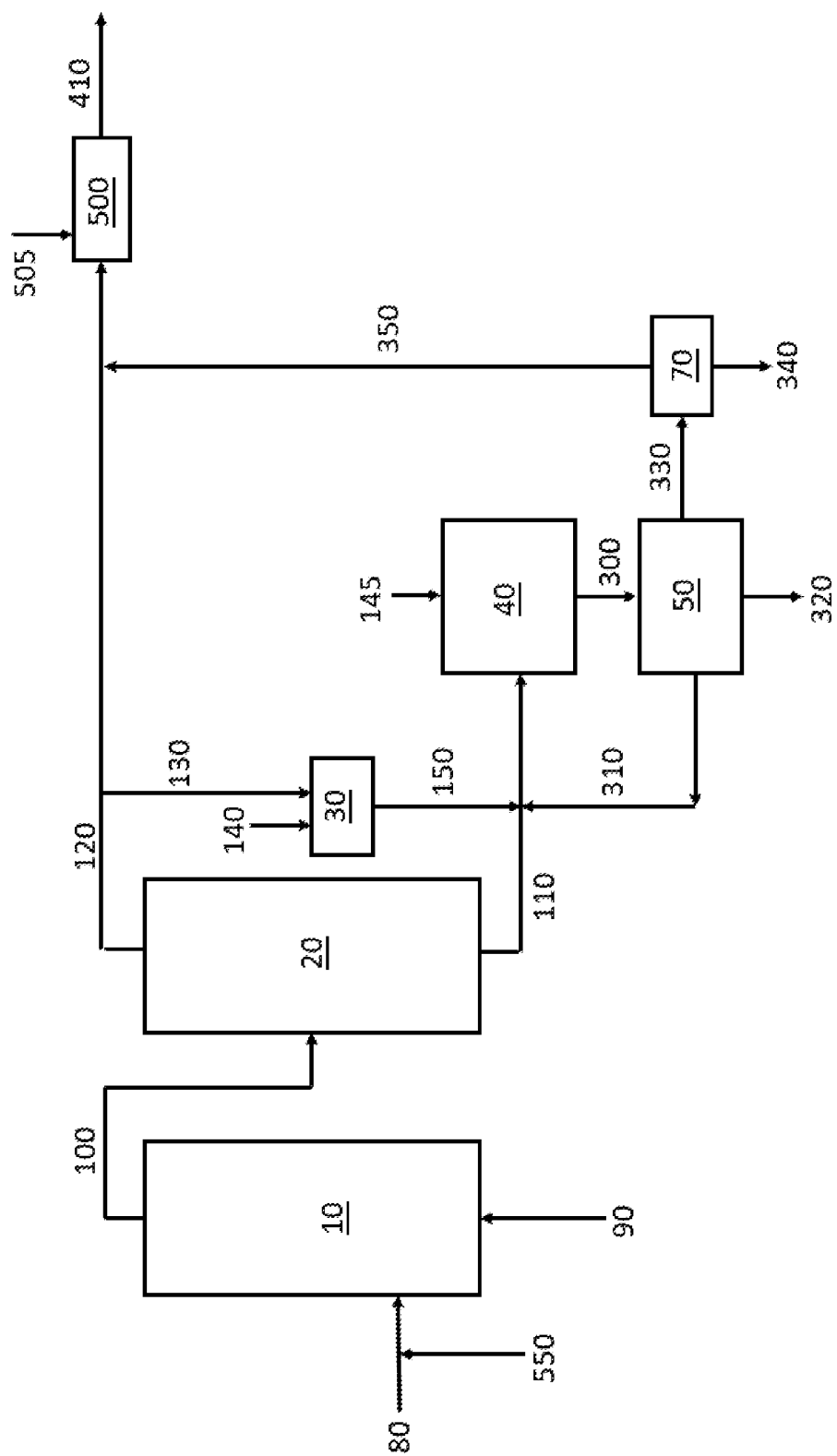
FIG. 3 is a graphic depiction of portions of a chemical complex according to some embodiments of the disclosure.

In embodiments of the disclosure, the chemical complex of the present disclosure, shown in an additional embodiment schematically in FIG. 3, includes, in cooperative arrangement, an ODH reactor 10, a quench tower or acetic acid scrubber 20, a first CO oxidation reactor 30 (as described herein), a vinyl acetate monomer (VAM) reactor 40, a VAM separation unit 50 and an inert removal unit 70.

ODH reactor 10 includes an ODH catalyst capable of catalyzing, in the presence of oxygen which may be introduced via oxygen line 80, the oxidative dehydrogenation of alkanes introduced via alkane line 90. The ODH reaction may also occur in the presence of an inert diluent, such as carbon dioxide, nitrogen, or steam, that is added to ensure the mixture of oxygen and hydrocarbon are outside of flammability limits. Determination of whether a mixture is outside of the flammability limits, for the prescribed temperature and pressure, is within the knowledge of the skilled worker. An ODH reaction that occurs within ODH reactor 10 may also produce, depending on the catalyst and the prevailing conditions within ODH reactor 10, a variety of other products which may include carbon dioxide, carbon monoxide, oxygenates, and water. These products leave ODH reactor 10, along with unreacted alkane, corresponding alkene, residual oxygen, carbon monoxide and inert diluent, if added, via ODH reactor product line 100.

ODH reactor product line 100 is directed to quench tower or acetic acid scrubber 20 which quenches the products from product line 100, and facilitates removal of acetic acid and water via quench tower bottom outlet 110. Unconverted lower alkane, corresponding alkene, unreacted oxygen, carbon dioxide, carbon monoxide, and inert diluent added to quench tower 20 exit through quench tower overhead line 120 and a portion are directed into first oxidation reactor 30 via first oxidation line 130.

First oxidation reactor 30 contains a group 11 metal with optional promoter and optional support as described above. First oxidation reactor 30 optionally includes first oxygen line 140 which can be used to provide an oxygen containing gas to first oxidation reactor 30. In first oxidation reactor 30, unreacted oxygen is reacted with carbon monoxide to form carbon dioxide and/or reacts acetylene to reduce or eliminate it. In first oxidation reactor 30, most or all of the unreacted oxygen is consumed. The remaining unconverted lower alkane, corresponding alkene, unreacted oxygen (if present), all or part of the carbon dioxide, carbon monoxide (if present), and inert diluent are directed to first ethylene product line 150 and combined with the acetic acid and water via quench tower bottom outlet 110 and conveyed to the VAM process.

In the VAM process, the contents of quench tower bottom outlet 110, which can include acetic, acid, ethylene, and optionally unreacted ethane, unconsumed oxygen-containing gas, water, carbon monoxide, carbon dioxide, and inert compounds are fed to VAM reactor 40, where acetic acid and ethylene are combined in the presence of a catalyst active for the production of vinyl acetate. VAM reactor 40 optionally includes VAM oxygen line 145 which can be used to provide an oxygen containing gas to VAM reactor 40 as described herein. Depending on the scale of the process, VAM reactor 40 may include either a single reactor or several reactors in parallel or in series. A VAM product stream 300 that includes vinyl acetate, water, optionally ethane, gaseous by-products and unreacted acetic acid and ethylene is withdrawn from VAM reactor 40 and is fed to VAM separation unit 50 where a VAM gaseous stream 330, which can include ethylene, and optionally ethane together with inert compounds, carbon monoxide and carbon dioxide is separated from water and acetic acid, which can alternatively be withdrawn overhead via first recycle line 310 and can be recycled to and mixed with the contents of quench tower bottom outlet 110 and provided to VAM reactor 40 as described above.

VAM liquid stream 320, which includes vinyl acetate, water, optionally unreacted acetic acid and optionally high boiling by-products of the process are withdrawn from the base of VAM separation unit 50 and vinyl acetate is isolated in state of the art equipment not shown. As a non-limiting example, the contents of VAM liquid stream 320 can be fed to a distillation column where vinyl acetate and water are removed as an azeotrope and acetic acid and the optional high boiling by-products are removed as a bleed from the base of the distillation column. The water in the overhead stream from the distillation column can be separated from the vinyl acetate in a decanter and a vinyl acetate product stream removed from decanter is purified by conventional means known in the art.

VAM gaseous stream 330 can be directed to inert removal unit 70, where carbon dioxide and other inert compounds are separated and directed to outlet stream 340 and ethylene and optionally ethane and remaining carbon monoxide are directed to ethylene containing stream 350 and combined into quench tower overhead line 120.

Quench tower overhead line 120 is fed to secondary oxidation reactor 500, which contains a group 11 metal with optional promoter and optional support as described above. In secondary oxidation reactor 500, unreacted oxygen is reacted with carbon monoxide to form carbon dioxide. In secondary oxidation reactor 500, most or all of the unreacted oxygen is consumed. Secondary oxidation reactor 500 optionally includes oxygen line 505 which can be used to provide an oxygen containing gas to secondary oxidation reactor 500. The remaining unconverted lower alkane, corresponding alkene, unreacted oxygen (if present), all or part of the carbon dioxide, carbon monoxide (if present), and inert diluent are directed to primary ethylene product line 410.

Figure 4:
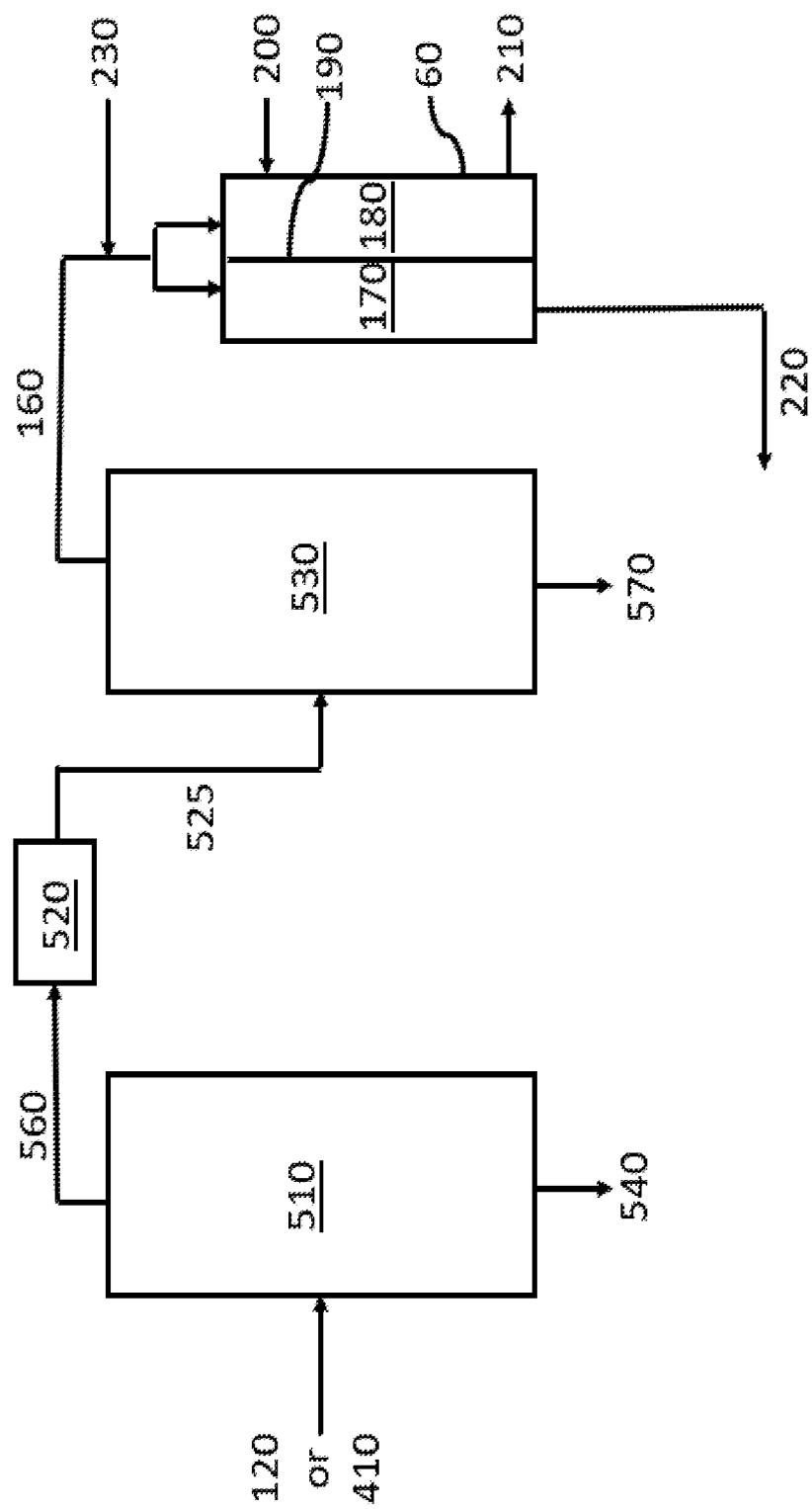
FIG. 4 is a graphic depiction of other portions of a chemical complex according to some embodiments of the disclosure.

As shown in FIG. 4, in the ethylene purification process either of primary ethylene product line 410 (as shown in FIGS. 2 and 3) or quench tower overhead line 120 (as shown in FIG. 1) are provided to the ethylene purification process, which can include an amine wash tower 510, a drier 520, a distillation tower 530, and an oxygen separation module 60. In many embodiments, primary ethylene product line 410 or quench tower overhead line 120 contain unconverted ethane, ethylene, optionally unreacted oxygen, all or part of the carbon dioxide, optionally carbon monoxide, and inert diluent, which are conveyed to amine wash tower 510.

Any carbon dioxide is isolated by amine wash tower 510, and captured via carbon dioxide bottom outlet 540 and may be sold, or, alternatively, may be recycled back to ODH reactor 10 via downstream recycle line 550 as shown in FIGS. 1, 2 and 3. Constituents introduced into amine wash tower 510, other than carbon dioxide, leave amine wash tower 510 through amine wash tower overhead line 560 and are passed through dryer 520 before being directed to distillation tower 530 via dryer line 525, where C2/C2+ hydrocarbons are isolated and removed via C2/C2+ hydrocarbons bottom outlet 570. The remainder includes mainly C1 hydrocarbons, including remaining inert diluent and carbon monoxide (if any), which leave distillation tower 530 via overhead stream 160 and is directed to oxygen separation module 60.

Oxygen separation module 60 includes a sealed vessel having a retentate side 170 and a permeate side 180, separated by oxygen transport membrane 190. Overhead stream 160 may be directed into either of retentate side 170 or permeate side 180. Optionally, a flow controlling means 260 (FIG. 6D) may be included that allows for flow into both sides at varying levels. In that instance an operator may choose what portion of the flow from overhead stream 160 enters retentate side 170 and what portion enters permeate side 180. Depending upon conditions an operator may switch between the two sides, to allow equivalent amounts to enter each side, or bias the amount directed to one of the two sides. Oxygen separation module 60 also includes air input 200 for the introduction of atmospheric air, or other oxygen containing gas, into retentate side 170. Combustion of products introduced into retentate side 170, due to the introduction of oxygen, may contribute to raising the temperature of oxygen transport membrane 190 to at least about 850° C. so that oxygen can pass from retentate side 170 to permeate side 180. Components within the atmospheric air, or other oxygen containing gas, other than oxygen, cannot pass from retentate side 170 to permeate side 180 and can only leave oxygen separation module 60 via exhaust 210.

As a result of oxygen passing from retentate side 170 to permeate side 180, there is separation of oxygen from atmospheric air, or other oxygen containing gas, introduced into retentate side 170. The result is production of oxygen enriched gas on permeate side 180, which is then directed via oxygen enriched bottom line 220 to ODH reactor 10, either directly or in combination with oxygen line 80 (as shown in FIGS. 1, 2 and 3). When overhead stream 160 is directed into retentate side 170 the degree of purity of oxygen in oxygen enriched bottom line 220 can approach 99%. Conversely, when overhead stream 160 is directed into permeate side 180 the degree of purity of oxygen in oxygen enriched bottom line 220 is lower, with an upper limit ranging from 80%-90% oxygen, the balance in the form of carbon dioxide, water, and remaining inert diluent, all of which do not affect the ODH reaction as contemplated by the present disclosure and can accompany the enriched oxygen into ODH reactor 10. Water and carbon dioxide can be removed by quench tower 20 and amine wash tower 510, respectively. In some embodiments of the disclosure, some or all of the carbon dioxide can be captured for sale as opposed to being flared where it contributes to greenhouse gas emissions. In other embodiments, when carbon dioxide is used in the ODH process, any carbon dioxide captured in the amine wash can be recycled back to ODH reactor 10.

Oxygen transport membrane 190 is temperature dependent, only allowing transport of oxygen when the temperature reaches at least about 850° C. In some embodiments, the components in overhead stream 160 by themselves are not capable, upon combustion in the presence of oxygen, to raise the temperature of oxygen transport membrane 190 to the required level. In this embodiment, the chemical complex of the present disclosure also includes fuel enhancement line 230, upstream of oxygen separation module 60, where combustible fuel, as a non-limiting example methane, may be added to supplement the combustible products from overhead stream 160.

Figure 6A:
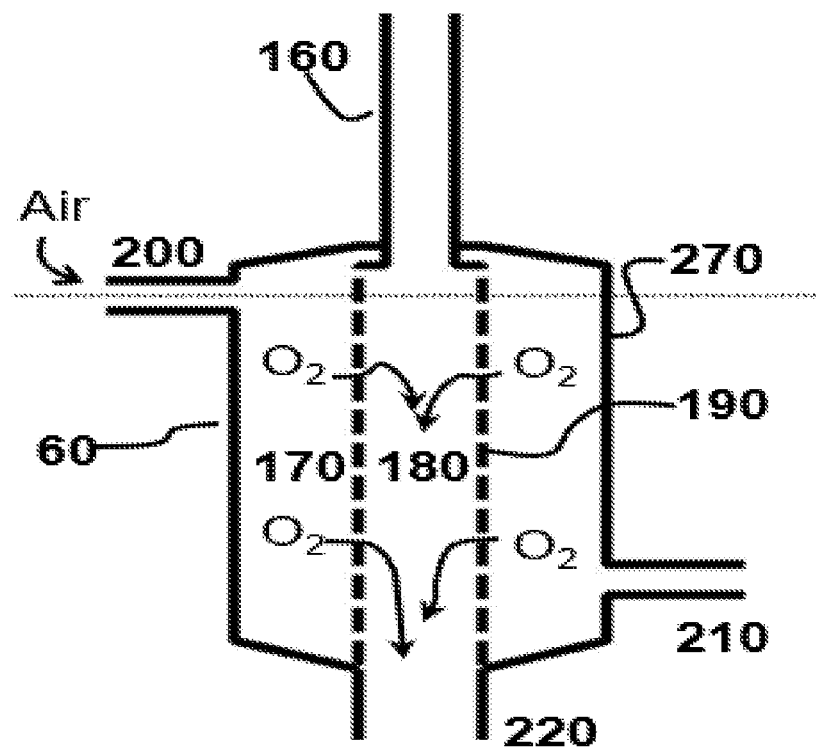
FIG. 6A—Schematic of embodiment of oxygen separation module where C1 hydrocarbon containing line is directed to permeate side.
Figure 6B:
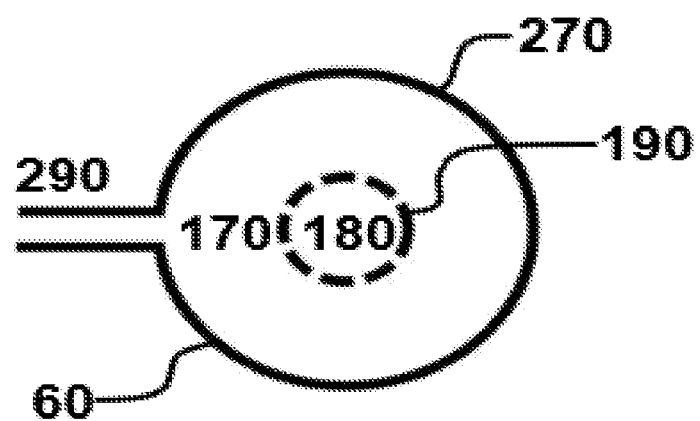
FIG. 6B—Cross section of oxygen separation module through dotted line present in FIGS. 6A, 6C, and 6D.
Figure 6C:
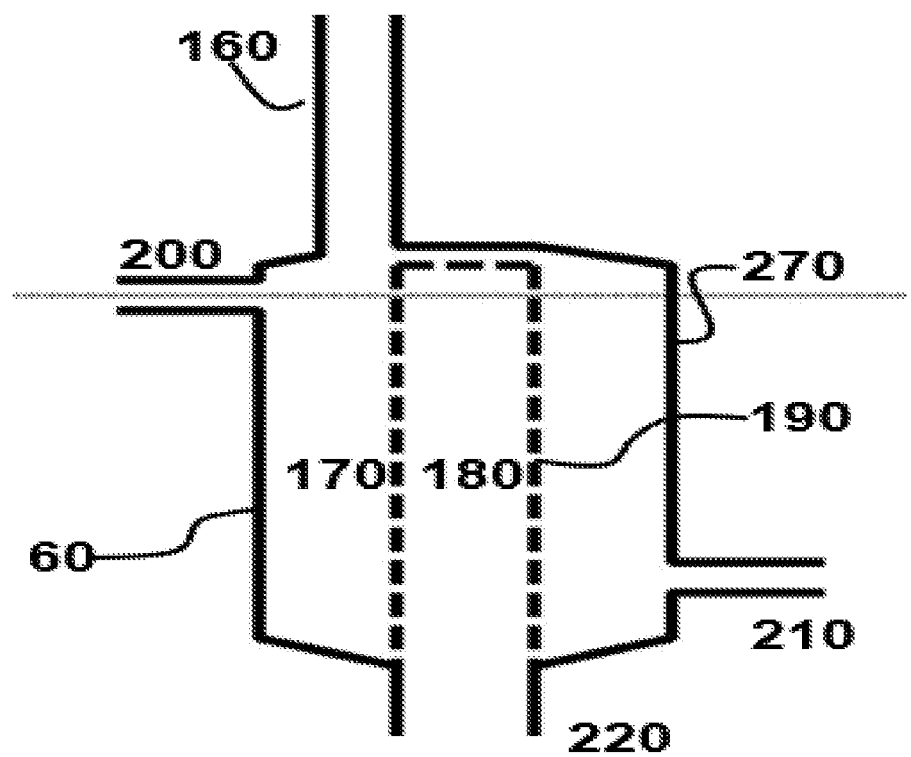
FIG. 6C—Schematic of embodiment of oxygen separation module where C1 hydrocarbon containing line is directed to the retentate side.

In an embodiment of the disclosure, the oxygen separation module 60 is a tube, as depicted schematically in FIG. 6B. The oxygen transport membrane 190 can be a tube and can fit inside a larger tube 270 which forms the outer wall of oxygen separation module 60. The annular space between the larger tube 270 and oxygen transport membrane 190 corresponds to the retentate side, while the space within oxygen transport membrane 190 corresponds to the permeate side. Material suitable for construction of the outer wall include those resistant to temperatures that exceed 850° C. and approach 1000° C., selection of which falls within the knowledge of the skilled worker.

The present disclosure contemplates the inlet for the overhead stream 160 entering the oxygen transport module 60 into either of the permeate side (FIG. 6A) or the retentate side (FIG. 6B). In some embodiments, oxygen separation module 60 can have C1 hydrocarbon containing line 290 directed to the retentate side 180. The present disclosure also contemplates the use of a valve 260 for switching between directing the overhead stream 160 to the retentate side 180 or the permeate side 170 (FIG. 6D). This would allow an operator to choose which of the sides, permeate or retentate, that the overhead stream is directed to.

Figure 5:
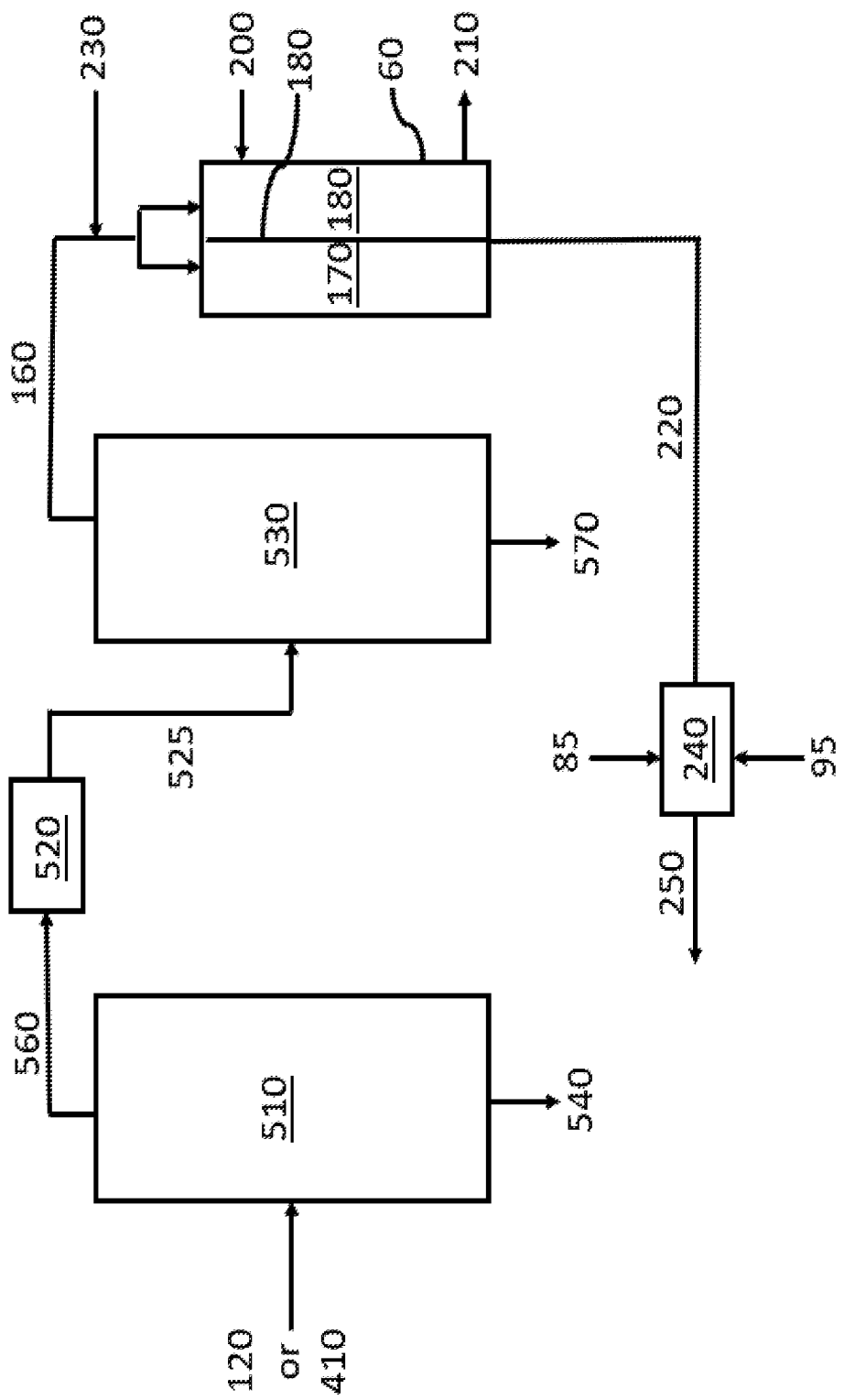
FIG. 5 is a graphic depiction of other portions of a chemical complex according to some embodiments of the disclosure.

In one embodiment of the disclosure there is a flooded gas mixer 240 (FIG. 5) upstream of ODH reactor 10 (FIGS. 1, 2 and 3). In this instance oxygen line 85 and ethane line 95 feed directly into flooded gas mixer 240. A homogeneous mixture that includes hydrocarbon and oxygen, and optionally an inert diluent, can be introduced into ODH reactor 10 from flooded gas mixer 240 via mixed line 250 (FIG. 5). Oxygen enriched bottom line 220 may feed directly into or in combination with oxygen line 70 into flooded gas mixer 240. Mixed line 250 can enter ODH reactor 10 at either or both of oxygen line 80 and ethane line 90.

The temperature of the contents within product line 100 (FIGS. 1, 2 and 3) in a typical ODH process can reach about 450° C. It can be desirable to lower the temperature of the stream before introduction into quench tower or acetic acid scrubber 20 as described above. In that instance, the present disclosure contemplates the use of a heat exchanger immediately downstream of each ODH reactor 10 and immediately upstream of quench tower 20. Use of a heat exchanger to lower temperatures in this fashion is well known in the art.

In embodiments of the disclosure, a concern for ODH processes is the mixing of a hydrocarbon with oxygen. Under certain conditions the mixture may be unstable and lead to an explosive event. U.S. published patent application No. 2018/0009662 ('662 application) published Jan. 11, 2018, titled "Inherently Safe Oxygen/Hydrocarbon Gas Mixer", discloses a means to mix a hydrocarbon containing gas with an oxygen containing gas in a flooded mixing vessel. By mixing in this way pockets of unstable compositions are surrounded by a non-flammable liquid so that even if an ignition event occurred it would be quenched immediately. Provided addition of the gases to the ODH reaction is controlled so that homogeneous mixtures fall outside of the flammability envelope, for the prescribed conditions with respect to temperature and pressure, the result is a safe homogeneous mixture of hydrocarbon and oxygen. The present disclosure may be supplemented with a flooded gas mixer as described in the '662 application.

The vinyl acetate monomer produced using the methods, apparatus and complexes disclosed herein can be polymerized to provide polyvinyl acetate (PVA). Vinyl acetate monomer can also be copolymerized with other monomers to provide various copolymers such as ethylene-vinyl acetate (EVA), vinyl acetate-acrylic acid (VA/AA), polyvinyl chloride-vinyl acetate (PVCA), and vinylpyrrolidone-vinyl acetate (Vp/Va Copolymer). In the above described non-limiting examples, the incorporated vinyl acetate repeat unit can be hydrolyzed to provide the corresponding vinyl alcohol repeat unit. As non-limiting examples, PVA can be partially hydrolyzed to provide a vinyl acetate-vinyl alcohol copolymer, completely hydrolyzed to provide polyvinyl alcohol, EVA can be partially hydrolyzed to provide an ethylene-vinyl acetate-vinyl alcohol terpolymer or completely hydrolyzed to provide an ethylene-vinyl alcohol copolymer.

In aspects of the disclosure, the vinyl alcohol repeat units can be reacted with butyraldehyde to form vinyl butyral repeat units. When all of the vinyl alcohol units have been reacted to form vinyl butyral repeat units, the resulting polymer is polyvinyl butyral or PVB.

A first aspect of the present disclosure relates to a method of converting ethane to ethylene and vinyl acetate that includes:

a. providing a first stream containing ethane and oxygen to an oxidative dehydrogenation reactor;

b. converting at least a portion of the ethane to ethylene and acetic acid in the oxidative dehydrogenation reactor to provide a second stream exiting the oxidative dehydrogenation reactor containing ethane, ethylene, acetic acid, oxygen, carbon monoxide and optionally acetylene;

c. separating at least a portion of the acetic acid from the second stream to provide an acetic acid containing stream and a third stream containing ethane, ethylene, oxygen and carbon monoxide;

d. providing the third stream to a CO Oxidation Reactor containing a catalyst that includes a group 11 metal and optionally a promoter containing $CeO_2$, $ZrO_2$ and combinations thereof to convert a least a portion of the carbon monoxide to carbon dioxide and reacting any acetylene in the third stream to produce a fourth stream containing ethane, ethylene and carbon dioxide; and e. providing a portion of the fourth stream and at least a portion of the acetic acid containing stream to a third reactor containing a catalyst that includes a metal selected from the group 10 and group 11 metals and combinations thereof to convert a least a portion of the ethylene and acetic acid to vinyl acetate.

In a second aspect, in the method according to the first aspect, the catalyst in the CO Oxidation Reactor is supported on $SiO_2$.

In a third aspect, in the method according to the first and second aspects, the fourth stream is essentially free of oxygen and/or substantially free of acetylene.

In a fourth aspect, in the method according to the first through third aspects, the oxidative dehydrogenation reactor contains an oxidative dehydrogenation catalyst that includes one or more mixed metal oxides selected from:

i) catalysts of the formula:

$$MO_aV_bTe_cNb_dPd_eO_f$$

wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to satisfy the valence state of the catalyst;

ii) catalysts of the formula:

$$Ni_gA_hB_iD_jO_f$$

wherein: g is a number from 0.1 to 0.9, in some cases from 0.3 to 0.9, in other cases from 0.5 to 0.85, in some instances 0.6 to 0.8; h is a number from 0.04 to 0.9; i is a number from 0 to 0.5; j is a number from 0 to 0.5; and f is a number to satisfy the valence state of the catalyst; A is chosen from Ti, Ta, V, Nb, Hf, W, Y, Zn, Zr, Si and Al or mixtures thereof; B is chosen from La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof; D is chosen from Ca, K, Mg, Li, Na, Sr, Ba, Cs, and Rb and mixtures thereof; and O is oxygen;

iii) catalysts of the formula:

$$MO_aE_kG_lO_f$$

wherein: E is chosen from Ba, Ca, Cr, Mn, Nb, Ta, Ti, Te, V, W and mixtures thereof; G is chosen from Bi, Ce, Co, Cu, Fe, K, Mg, V, Ni, P, Pb, Sb, Si, Sn, Ti, U, and mixtures thereof; a=1; k is 0 to 2; l=0 to 2, with the proviso that the total value of I for Co, Ni, Fe and mixtures thereof is less than 0.5; and f is a number to satisfy the valence state of the catalyst;

iv) catalysts of the formula:

$$V_mMo_nNb_oTe_pMe_qO_f$$

wherein: Me is chosen from Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to satisfy the valence state of the catalyst;

v) catalysts of the formula:

$$MO_aV_rX_sY_tZ_uM_vO_f$$

wherein: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to satisfy the valence state of the catalyst.

vi) a mixed metal oxide having the empirical formula:

$$Mo_{6.5-7.0}V_3O_d$$

where d is a number to satisfy the valence of the oxide.

vii) a mixed metal oxide having the empirical formula:

$$Mo_{6.25-7.25}V_3O_d$$

where d is a number to satisfy the valence of the oxide.

In a fifth aspect, in the method according to the first through forth aspects, the first stream contains one or more inert diluents and an oxygen containing gas.

In a sixth aspect, in the method according to the first through fifth aspects, the second stream contains ethane; ethylene; oxygen; one or more inert diluents; carbon dioxide; carbon monoxide; acetic acid; water and optionally acetylene.

In a seventh aspect, in the method according to the first through sixth aspects, the one or more oxidative dehydrogenation reactors include a single fixed bed type reactor, a single fluidized bed type reactor, a moving bed reactor, and/or a swing bed type reactor.

In an eighth aspect, in the method according to the first through seventh aspects, the group 11 metal in the CO Oxidation Reactor is selected from copper, silver, gold and combinations thereof.

In a ninth aspect, in the method according to the first through eighth aspects, the catalyst in the CO Oxidation Reactor includes $Ag/SiO_2$, $AgCeO_2/SiO_2$, $AgZrO_2/SiO_2$, $Cu/SiO_2$, $CuCeO_2/SiO_2$, $CuZrO_2/SiO_2$, $CuCo_3O_4/SiO_2$ and combinations thereof.

In a tenth aspect, in the method according to the first through ninth aspects, the group 11 metal in the third reactor is selected from copper, silver, gold and combinations thereof.

In a eleventh aspect, in the method according to the first through tenth aspects, the group 10 metal in the third reactor is selected from nickel, palladium, platinum and combinations thereof.

In a twelfth aspect, in the method according to the first through eleventh aspects, the temperature in the CO Oxidation Reactor is from about 40 to about 100° C.

A thirteenth aspect of the present disclosure relates to a chemical complex for oxidative dehydrogenation of ethane, the chemical complex includes in cooperative arrangement:

i) one or more oxidative dehydrogenation reactors, that include an oxidative dehydrogenation catalyst and designed to accept, optionally in the presence of an inert diluent, an oxygen containing gas and an ethane containing gas, and to produce a product stream containing ethylene, acetic acid, oxygen, carbon monoxide and optionally acetylene;

ii) a quench tower for quenching the product stream and for generating an acetic acid stream containing acetic acid and an ethylene product stream containing ethylene, carbon monoxide, oxygen and optionally acetylene;

iii) a carbon monoxide oxidation reactor for oxidizing carbon monoxide to carbon dioxide and eliminating acetylene in the ethylene product stream; and iv) a vinyl acetate monomer (VAM) reactor configured to accept a portion of the ethylene product stream and at least a portion of the acetic acid stream and including a VAM catalyst to produce a VAM product stream that includes vinyl acetate monomer.

In a fourteenth aspect, in the method according to the thirteenth aspect the oxidative dehydrogenation catalyst includes one or more mixed metal oxides chosen from:

i) catalysts of the formula:

$$MO_a V_b Te_c Nb_d Pd_e O_f$$

wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to satisfy the valence state of the catalyst;

ii) catalysts of the formula:

$$Ni_g A_h B_i D_j O_f$$

wherein: g is a number from 0.1 to 0.9, in some cases from 0.3 to 0.9, in other cases from 0.5 to 0.85, in some instances 0.6 to 0.8; h is a number from 0.04 to 0.9; i is a number from 0 to 0.5; j is a number from 0 to 0.5; and f is a number to satisfy the valence state of the catalyst; A is chosen from Ti, Ta, V, Nb, Hf, W, Y, Zn, Zr, Si and Al or mixtures thereof; B is chosen from La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof; D is chosen from Ca, K, Mg, Li, Na, Sr, Ba, Cs, and Rb and mixtures thereof; and O is oxygen;

iii) catalysts of the formula:

$$MO_a E_k G_l O_f$$

wherein: E is chosen from Ba, Ca, Cr, Mn, Nb, Ta, Ti, Te, V, W and mixtures thereof; G is chosen from Bi, Ce, Co, Cu, Fe, K, Mg, V, Ni, P, Pb, Sb, Si, Sn, Ti, U, and mixtures thereof; a=1; k is 0 to 2; l=0 to 2, with the proviso that the total value of l for Co, Ni, Fe and mixtures thereof is less than 0.5; and f is a number to satisfy the valence state of the catalyst;

iv) catalysts of the formula:

$$V_m Mo_n Nb_o Te_p Me_q O_f$$

wherein: Me is a metal chosen from Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to satisfy the valence state of the catalyst; and v) catalysts of the formula:

$$MO_a V_r X_s Y_t Z_u M_v O_f$$

wherein: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to satisfy the valence state of the catalyst.

vi) a mixed metal oxide having the empirical formula:

$$Mo_{6.5-7.0} V_3 O_d$$

where d is a number to satisfy the valence of the oxide.

vii) a mixed metal oxide having the empirical formula:

$$Mo_{6.25-7.25} V_3 O_d$$

where d is a number to satisfy the valence of the oxide.

In a fifteenth aspect, in the method according to the thirteenth and fourteenth aspects, the one or more oxidative dehydrogenation reactors include a single fixed bed type reactor, a single fluidized bed type reactor, a moving bed reactor, and/or a swing bed type reactor.

In a sixteenth aspect, in the method according to the thirteenth through fifteenth aspects, the one or more oxidative dehydrogenation reactors include more than one oxidative dehydrogenation reactors, each including the same or different oxidative dehydrogenation catalysts, connected in series, and wherein the product stream from each oxidative dehydrogenation reactor except the last oxidative dehydrogenation reactor in the series is fed into a downstream oxidative dehydrogenation reactor.

In a seventeenth aspect, in the method according to the thirteenth through sixteenth aspects, the at least one oxidative dehydrogenation reactor includes more than one oxidative dehydrogenation reactor connected in parallel and each including the same or different oxidative dehydrogenation catalyst.

In a eighteenth aspect, in the method according to the thirteenth through seventeenth aspects, unreacted ethane is directed back to the at least one oxidative dehydrogenation reactor as part of the ethane containing gas.

In an nineteenth aspect, in the method according to the thirteenth through eighteenth aspects, the carbon monoxide oxidation reactor contains a catalyst that includes a group 11 metal.

In a twentieth aspect, in the method according to the thirteenth through nineteenth aspects, the group 11 metal is selected from copper, silver, gold and combinations thereof.

In a twenty-first aspect, in the method according to the thirteenth through twentieth aspects, the group 11 metal is silver or copper.

In a twenty-second aspect, in the method according to the thirteenth through twenty-first aspects, the carbon monoxide oxidation reactor contains a catalyst that includes $Ag/SiO_2$, $AgCe/SiO_2$, $AgZr/SiO_2$, $AgCeO_2/SiO_2$, $AgZrO_2/SiO_2$, $Cu/SiO_2$, $CuCeO_2/SiO_2$, $CuZrO_2/SiO_2$, $CuCo_3O_4/SiO_2$ and combinations thereof.

In a twenty-third aspect, in the method according to the thirteenth through twenty-second aspects, the stream entering the carbon monoxide oxidation reactor includes from 100 ppm to 5 wt. % oxygen and optionally from 1 vppm to 1000 vppm acetylene.

In a twenty-fourth aspect, in the method according to the thirteenth through twenty-third aspects, the stream exiting the carbon monoxide oxidation reactor is essentially free of oxygen and/or substantially free of acetylene.

In a twenty-fifth aspect, in the method according to the thirteenth through twenty-fourth aspects, the amount of carbon dioxide in the stream entering the carbon monoxide oxidation reactor is less than the amount of carbon dioxide in the stream exiting the carbon monoxide oxidation reactor.

In a twenty-sixth aspect, in the method according to the thirteenth through twenty-fifth aspects, the amount of carbon monoxide in the stream entering the carbon monoxide oxidation reactor is greater than the amount of carbon monoxide in the stream exiting the carbon monoxide oxidation reactor.

In a twenty-seventh aspect, in the method according to the thirteenth through twenty-sixth aspects, the temperature in the carbon monoxide oxidation reactor is from 40 to 100° C.

In a twenty-eighth aspect, in the method according to the thirteenth through twenty-seventh aspects, the VAM reactor contains a catalyst that includes a metal selected from the group 10 and group 11 metals and combinations thereof.

In a twenty-ninth aspect, in the method according to the thirteenth through twenty-eighth aspects, the group 11 metal in the VAM reactor is selected from copper, silver, gold and combinations thereof.

In a thirtieth aspect, in the method according to the thirteenth through twenty-ninth aspects, the group 10 metal in the VAM reactor is selected from nickel, palladium, platinum and combinations thereof.

In a thirty-first aspect, in the method according to the thirteenth through thirtieth aspects, a portion of the ethylene is used to make olefin derivatives.

In a thirty-second aspect, in the method according to the thirteenth through thirty-first aspects, the olefin derivatives are selected from polyethylene, polypropylene, ethylene oxide, propylene oxide, polyethylene oxide, polypropylene oxide, thermoplastic elastomers, thermoplastic olefins and blends and combinations thereof.

In a thirty-third aspect, in the method according to the thirteenth through thirty-second aspects, the portion of ethylene is used to make polyethylene.

In a thirty-fourth aspect, in the method according to the thirteenth through thirty-third aspects, the polyethylene is selected from homopolymers of ethylene, copolymers of ethylene and α-olefins, HDPE, MDPE, LDPE, LLDPE, VLDPE and combinations and blends thereof.

In a thirty-fifth aspect, in the method according to the thirteenth through thirty-fourth aspects, the polyethylene is produced using one or more processes selected from gas phase polyethylene processes, high pressure polyethylene processes, low pressure polyethylene processes, solution polyethylene processes, slurry polyethylene processes and combinations thereon in parallel and/or series reactor configurations.

In a thirty-sixth aspect, the vinyl acetate monomer produced using any of aspects one through thirty-five can be polymerized to provide polyvinyl acetate (PVA).

In a thirty-seventh aspect, all, or at least a portion of the PVA in the thirty-sixth aspect can be hydrolyzed to provide a vinyl acetate-vinyl alcohol copolymer or polyvinyl alcohol.

In a thirty-eighth aspect, the vinyl acetate monomer produced using any of aspects one through thirty-five can be copolymerized with other monomers to provide various copolymers such as ethylene-vinyl acetate (EVA), vinyl acetate-acrylic acid (VA/AA), polyvinyl chloride-vinyl acetate (PVCA), and vinylpyrrolidone-vinyl acetate (Vp/Va Copolymer).

In a thirty-ninth aspect, the copolymers can be hydrolyzed to convert all or some of the vinyl acetate repeat units to the corresponding vinyl alcohol repeat units.

In a fortieth aspect, the EVA in the thirty seventh aspect can be partially hydrolyzed to provide an ethylene-vinyl acetate-vinyl alcohol terpolymer or completely hydrolyzed to provide an ethylene-vinyl alcohol copolymer.

In a forty-first aspect, the vinyl alcohol repeat units in the thirty-seventh aspect can be reacted with butyraldehyde to form vinyl butyral repeat units. When all of the vinyl alcohol units have been reacted to form vinyl butyral repeat units, the resulting polymer is polyvinyl butyral or PVB.

The following examples are intended to aid in understanding the present disclosure, however, in no way, should these examples be interpreted as limiting the scope thereof.

EXAMPLES

Example 1 (ODH Process)

The effect of altering the amount of steam injected into an ODH process on the carbon dioxide output was demonstrated using two fixed bed reactors, connected in series. The catalyst present in each of the reactors was a mixture of several batches of a mixed metal oxide catalyst of the formula: $Mo_{1.0}V_{0.30-0.50}Te_{0.10-0.20}Nb_{0.10-0.20}O_d$, where the subscripts represent the range of atomic amounts of each element, relative to Mo, present in the individual batches, and d represents the highest oxidation state of the metal oxides present in the catalyst. Ethane, carbon dioxide, and oxygen were premixed before addition of water, followed by preheating with the entire composition being fed to the first of the two reactors. The preheating step was necessary to ensure the water added was converted to steam before injection into the reactor. Output from the first reactor was sent directly into the CO Oxidation Reactor without addition of new reactants. For each reactor, the temperature was held in the range of 334-338° C. at ambient pressure. The process was run continuously over a period of three days.

The relative amounts of ethane, carbon dioxide, and oxygen remained the same while the flow rate of steam added to reactor was altered. The relative amounts of ethane, carbon dioxide, and oxygen added to the first reactor were 33, 54, and 13 respectively. The gas hourly space velocity (GHSV) was kept constant at about 610 $h^{-1}$. Flow rates of reaction ethane, carbon dioxide and oxygen were altered accordingly to maintain a gas hourly space velocity of about 610 $h^{-1}$ after altering the amount of steam added to reactor.

Steam was added indirectly as water with the ethane, carbon dioxide and oxygen mixture. The amount of water added to the mixture before entering the first reactor was varied, starting with no water and increasing in increments up to a flow rate of 1.0 $cm^3$/min. For each flow rate of water added to the mixture, a corresponding weight % of steam in the total feed mixture was calculated. Table 1 shows the effect that changing the amount of steam added to the reactor had on output of carbon dioxide, carbon monoxide, and acetic acid. The output of the components was measured as normalized selectivity, according to the formula:

$$X \text{ selectivitty (Wt \%)} = \frac{\text{net mass flow rate } X(\text{g } X/\text{hr})}{\frac{\text{mass flow rate } C_2H_6 \text{ (g } C_2H_6/\text{min)}}{C_2H_6 \text{ molecular weight (g } C_2H_6/\text{mol } C_2H_6)}} \times$$

$$X \text{ molecular weight } \left(g\frac{X}{\text{mol}}X\right) \times$$

$$\frac{N \text{ mol equivalent of compound } X}{1 \text{ mol } C_2H_6}$$

where X refers to one of ethylene, $CO_2$, CO, and acetic acid.

Results listed in Table 1 were averaged from two or more experimental runs at each of the prescribed conditions. The results demonstrate that increasing the flow rate of water added to the mixture and corresponding increase in the weight % of steam added to the reactor led to a decrease in the carbon selectivity. A carbon dioxide negative process was seen when the water was added at a flow rate of 1.0 cm$^3$/min, which corresponds to 39 weight % of steam added. Also, reverting back to no steam added followed by increasing to 39 weight % resulted in the carbon dioxide selectivity going positive back to negative. Finally, it should be noted that increasing the steam resulted in a higher production of acetic acid and also was accompanied by a higher conversion rate of ethane.

TABLE 1

Normalized Selectivity of ODH Products in Response to Changes in Steam Added to the Reactor

| Experiment Number | Water (not steam) Added (cm$^3$/min) | Steam Added (wt %) | Ethane Conversion (%) | Selectivity (wt %) | | | |
|---|---|---|---|---|---|---|---|
| | | | | Ethylene | CO$_2$ | CO | Acetic acid |
| 1-1 | 0.0 | 0 | 38.4 | 83.0 | 6.30 | 8.1 | 2.6 |
| 1-2 | 0.1 | 3 | 41.6 | 82.0 | 6.0 | 7.7 | 4.3 |
| 1-3 | 0.4 | 13 | 43.5 | 79.2 | 6.0 | 7.0 | 7.7 |
| 1-4 | 0.8 | 29 | 45.8 | 79.2 | 3.6 | 6.8 | 10.4 |
| 1-5 | 1.0 | 39 | 49.8 | 88.7 | −9.8 | 7.3 | 13.8 |
| 1-6 | 0.0 | 0 | 37.9 | 84.2 | 4.4 | 7.8 | 3.7 |
| 1-7 | 1.0 | 39 | 50.0 | 90.4 | −10.5 | 7.3 | 12.8 |

An acetic acid stream was created by condensing acetic acid from the stream produced from the ODH processes shown in Table 1, which also provided an ethylene stream containing the more volatile components.

Examples 2-6 (CO Selective Oxidation Process)

Experimental Reactor Unit (ERU) Setup

Figure 7:
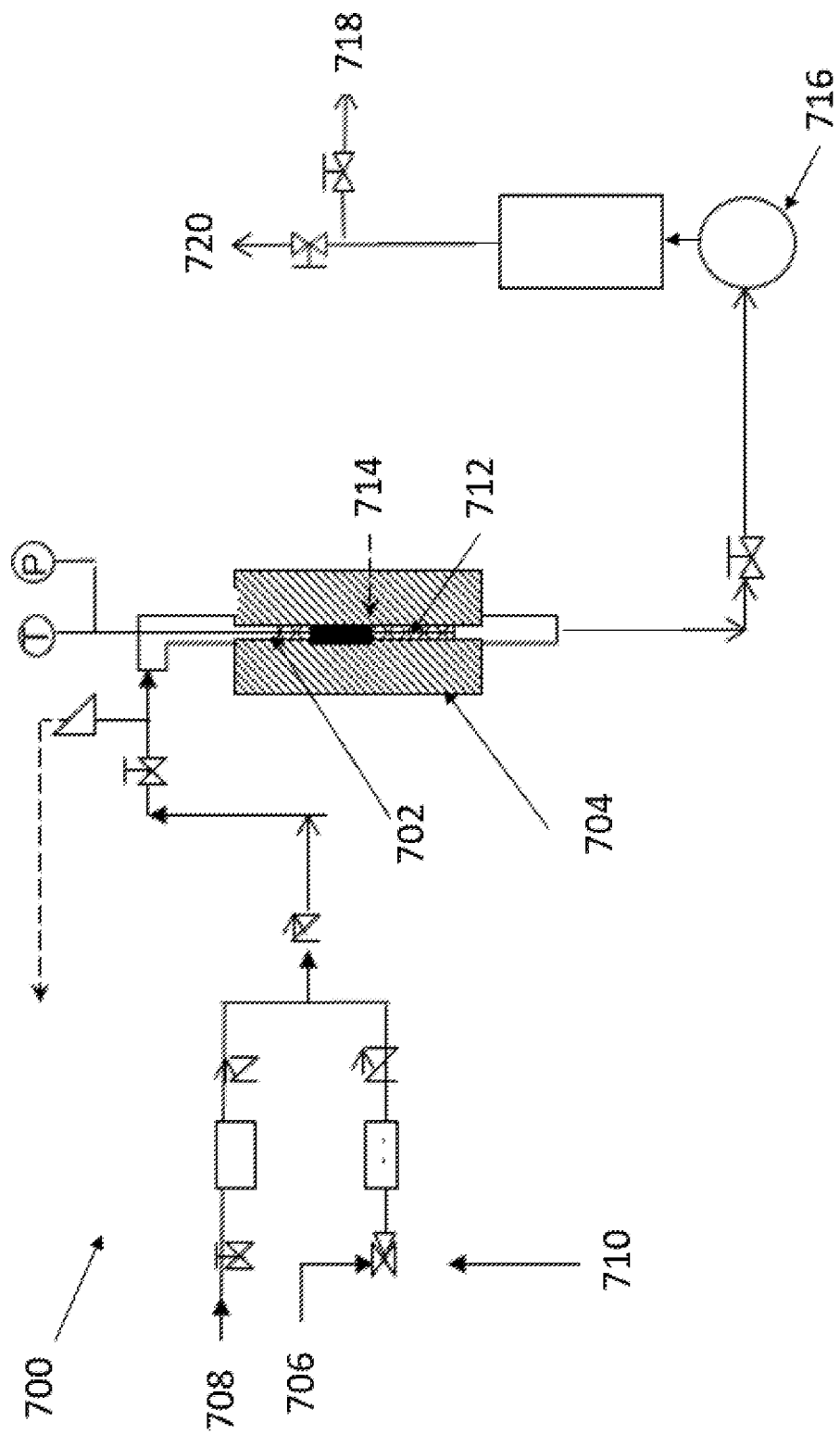
FIG. 7—Schematic of the experimental reactor unit as described in the examples.

The ERU was used to produce feed gas for evaluating catalysts according to the disclosure. The apparatus (700 in FIG. 7) consists of fixed bed tube reactor, 702, which is surrounded by two-zone electric heater 704. Reactor 702 is a 316L stainless steel tube which has an outside diameter of 0.5 inches (about 1.25 cm) and inside diameter of 0.4 inches (about 1 cm) and a length of 14.96 inches (about 38 cm). Two main feed gas lines are attached to reactor 702; one line 706 is dedicated for a bulk nitrogen purge gas and the other line 708 is connected to a dual solenoid valve, which can be switched from OOH process feed gas (gas mixture of ethane/oxygen/Nitrogen at a molar ratio of about 36/18/46) to compressed air when regenerating catalyst bed 714.

For safety reasons the unit is programmed in a way that prevents air from mixing with the feed gas. This is accomplished through safety interlocks and a mandatory 15-minute nitrogen purge of the reactor when switching between feed gas 706 and air 710. The flow of gases is controlled by mass flow controllers. A 6-point thermocouple 712 is inserted through reactor 702, which is used to measure and control the temperature within catalyst bed 714. The catalyst is loaded in the middle zone of reactor 702 and located in between points 3 and 4 of thermocouple 712, which are the reaction temperature control points. The remaining 4 points of thermocouple 712 are used for monitoring purposes. Catalyst bed 714 consists of a one to one volume ratio of catalyst to quartz sand, a total of 3 ml. The rest of reactor 702, below and above catalyst bed 714 is packed with 100% quartz sand and the load is secured with glass wool on the top and the bottom of reactor 702. A glass tight sealed condenser 716 is located after reactor 702 at room temperature to collect water/acidic acid and the gas product can flow to either vent 720 or sampling loop/vent 718 by a three-way solenoid valve.

CO Selective Oxidation Catalyst Testing Reactor

A 316L stainless steel tube with the following dimensions was used to test CO selective oxidation catalysts:
Outside diameter: 0.25 inches (about 0.63 cm)
Wall thickness: 0.028 inches (about 0.07 cm)
Catalyst bed height: 2 inches (about 5 cm)

The total weight of the catalyst is recorded for each catalyst, which was tested. The flow of gases is controlled by the mass flow controllers on ERU. The product gas from ERU is directly fed in to the CO selective oxidation catalyst testing reactor ("Testing Rector"). The Testing Reactor was placed in a precision heating oven, in which the temperature was controlled within less than 0.5° C. There were no thermocouples inside the reactor catalyst bed itself, as a result, the oven temperature was recorded as the catalyst testing temperature. The catalyst bed consisted of approximately 1 g of catalyst supported between two layers of quartz wool. The effluent from the reactor was continuously provided for gas chromatography analysis.

AgCe on Silica Catalyst Sample

SYLOPOL® 2408 silica (W.R. Grace, surface area: 316 m$^2$/g, pore volume: 1.54 cc/g, 20 g) was impregnated with a solution (40 ml) of Ce(NO$_3$)$_3$.6H$_2$O (2.80 g) and X. The impregnated silica was dried at 90° C. overnight and was calcined in air at 500° C. for 6 hours.

X=AgNO$_3$, 103 mL of 0.1N solution. The solution was concentrated to about 20 ml and mixed with Ce(NO$_3$)$_3$.6H$_2$O. Distilled water was added to make 40 ml.

The catalyst made was CeAg oxide on silica with CeO$_2$: 5 wt %, Ag: 5 wt %.

CuCe on Silica Catalyst Sample

SYLOPOL 2408 silica (20 g) was impregnated with a solution (40 ml) of Ce(NO$_3$)$_3$.6H$_2$O (2.80 g) and Y. The impregnated silica was dried at 90° C. overnight and was calcined in air at 500° C. for 6 hours.

Y=Cu(CH$_3$COO)$_2$, 3.17 g. The solution was concentrated to about 20 ml and was mixed with Ce(NO$_3$)$_3$.6H$_2$O. Distilled water was added to make 40 ml.

The catalyst made was CeCu oxide on silica with CeO$_2$: 5 wt %, Cu: 5 wt %.

MnCe on Silica Catalyst Sample

SYLOPOL 2408 silica (20 g) was impregnated with a solution (40 ml) of Ce(NO$_3$)$_3$.6H$_2$O (2.80 g) and Z. The impregnated silica was dried at 90° C. overnight and was calcined in air at 500° C. for 6 hours.

Z=MnCL$_2$.4H$_2$O, 4.0 g. The solution was concentrated to about 20 ml and was mixed with Ce(NO$_3$)$_3$.6H$_2$O. Distilled water was added to make 40 ml.

The catalyst made was CeMn oxide on silica with CeO$_2$: 5 wt %, Mn: 5 wt %.

CrCe on Silica Catalyst Sample

SYLOPOL 2408 silica (20 g) was impregnated with a solution (40 ml) of $Ce(NO_3)_3 \cdot 6H_2O$ (2.80 g) and W. The impregnated silica was dried at 90° C. overnight and was calcined in air at 500° C. for 6 hours.

W=$Cr(NO_3)_3 \cdot 9H_2O$, 6.98 g. The solution was concentrated to about 20 ml and was mixed with $Ce(NO_3)_3 \cdot 6H_2O$. Distilled water was added to make 40 ml.

The catalyst made was CeCr oxide on silica with $CeO_2$: 5 wt %, Cr: 5 wt %.

the reactor. 1 g was the value for the catalyst weight used for the long term test calculations. In this example, the ODH catalyst used to produce the feed for this example was a MoVOx based catalyst used as described in Example 2. In this example, the feed sample to the selective CO oxidation reactor was taken twice at the beginning and at the end of the test in order to confirm the composition of the feed. The test was executed at 110° C. process temperature, 0 psig reactor outlet pressure, gas hourly space velocity of approximately 3000 $h^{-1}$. The results are summarized in the table below.

|  | Time on stream H | $C_2H_6$ Vol. % | $C_2H_4$ Vol. % | $O_2$ Vol. % | $CO_2$ Vol. % | $N_2$ Vol. % | CO Vol. % | $C_2H_2$ vppm | $O_2$ removed % |
|---|---|---|---|---|---|---|---|---|---|
| Feed | 0 | 23.283 | 12.448 | 0.539 | 2.820 | 55.747 | 5.163 | 67 |  |
| Product | 3 | 23.237 | 12.529 | 0.222 | 2.880 | 55.957 | 5.176 | <1 | 58.860 |
|  | 27 | 24.138 | 13.005 | 0.388 | 2.804 | 54.692 | 4.974 | <1 |  |
|  | 39 | 23.440 | 12.633 | 0.297 | 2.824 | 55.725 | 5.082 | <1 |  |
|  | 43 | 23.841 | 12.810 | 0.416 | 2.788 | 55.132 | 5.013 | <1 |  |
|  | 47 | 23.916 | 12.818 | 0.513 | 2.773 | 54.995 | 4.985 | <1 |  |
|  | 54 | 23.436 | 12.543 | 0.560 | 2.792 | 55.651 | 5.019 | <1 |  |
|  | 65 | 23.233 | 12.434 | 0.434 | 2.824 | 55.997 | 5.079 | <1 |  |
|  | 69 | 23.911 | 12.767 | 0.531 | 2.771 | 55.041 | 4.979 | <1 |  |
|  | 73 | 23.823 | 12.704 | 0.645 | 2.765 | 55.097 | 4.967 | <1 |  |
|  | 76 | 24.174 | 12.838 | 0.726 | 2.727 | 54.640 | 4.896 | <1 |  |
|  | 80 | 23.236 | 12.328 | 0.760 | 2.784 | 55.888 | 5.004 | <1 |  |
|  | 91 | 23.355 | 12.404 | 0.547 | 2.803 | 55.849 | 5.042 | <1 |  |
|  | 95 | 24.354 | 12.898 | 0.696 | 2.723 | 54.436 | 4.893 | <1 | 41.245 |
| Feed-end | 96 | 23.693 | 12.579 | 1.185 | 2.596 | 53.892 | 6.056 | 70 |  |

"$O_2$ removed" value is calculated as follows:

$$V_{O2} = \frac{(C_{O2feed} - C_{O2product}) * 100\%}{C_{O2feed}}$$

Where:
$V_{O2}$-the value of "$O_2$ removed"
C-volumetric concentration of oxygen in the feed and product gasses Example 2

AgCe on Silica Catalyst Testing

The ODH process was run using the ERU and catalyst MoVOx to provide the feed for this example. 0.15 g of AgCe catalyst was used for this test at a gas hourly space velocity of approximately 5000 h-1, 0 psig on the reactor outlet, at 75° C. process temperature. The results are shown in the table below.

|  | $C_2H_6$ Vol. % | $C_2H_4$ Vol. % | $O_2$ Vol. % | $N_2$ Vol. % | $CO_2$ Vol. % | CO Vol. % | $C_2H_2$ vppm |
|---|---|---|---|---|---|---|---|
| Feed | 20.59 | 15.84 | 0.48 | 55.09 | 2.32 | 5.67 | 220 |
| Product | 21.44 | 16.53 | 0.06 | 54.06 | 3.37 | 4.50 | <1 |

The data show that the AgCe catalyst demonstrates excellent oxygen removal properties via selective oxidation of CO to $CO_2$, which can be seen from noticeable reduction of CO in the product gas and increase in all of the other compounds. It is noteworthy that acetylene is also fully oxidized and was not detected in the product gas from the Testing Reactor.

Example 3

1.7 g of AgCe catalyst was used for this test, with approximately 1 g of the catalyst present in the hot zone of Because the composition of the feed to the selective CO oxidation reactor was changing gradually over the term of the experiment, accurate values for removed oxygen could only be calculated at the very beginning and at the very end of the run. The data show that even though the catalyst had very stable activity toward acetylene oxidation through the whole duration of the run, the activity toward $O_2$ removal via selective CO oxidation gradually decreased over the duration of the run. Generally, the amount of CO and $O_2$ in the product stream was less than in the feed stream and the amount of $CO_2$ in the product stream was greater than the amount in the feed stream.

Example 4

The ODH process of Example 2 was used to provide the feed for this example. 0.35 g of AgCe catalyst, regenerated via oxidation, was used for this test. The test was executed at 110° C. process temperature, 0 psig reactor outlet pressure, gas hourly space velocity of approximately 3000 $h^{-1}$. The results are shown in the table below.

|  | $C_2H_6$ Vol.-% | $C_2H_4$ Vol.-% | $O_2$ Vol.-% | $N_2$ Vol.-% | $CO_2$ Vol.-% | CO Vol.-% | $C_2H_2$ vppm |
|---|---|---|---|---|---|---|---|
| Feed | 22.318 | 12.963 | 0.176 | 56.020 | 2.643 | 5.879 | 90 |
| Product | 22.151 | 12.883 | 0.027 | 56.374 | 2.650 | 5.915 | <1 |

The data show that the AgCe catalyst was successfully regenerated. Acetylene was reduced to undetectable levels and oxygen levels in the product stream were less than in the product stream.

Example 5

The ODH process of Example 2 was used to provide the feed for this example. 1.22 g of fresh CuCe catalyst was used for this test. The test was executed at 120° C. process temperature, 0 psig reactor outlet pressure, gas hourly space velocity of approximately 3000 h$^{-1}$. The results are summarized in the table below.

|  | $C_2H_6$ Vol.-% | $C_2H_4$ Vol.-% | $O_2$ Vol.-% | $N_2$ Vol.-% | $CO_2$ Vol.-% | CO Vol.-% | $C_2H_2$ vppm |
|---|---|---|---|---|---|---|---|
| Feed | 26.295 | 14.789 | 0.27915 | 51.35468 | 2.321394 | 4.960777 | 70 |
| Product | 25.268 | 14.453 | 0.024041 | 52.69556 | 2.532941 | 5.026455 | <1 |

The data show that the CuCe catalyst exhibits similar properties to the AgCe catalyst. CuCe catalyzes the reaction of selective oxidation of CO to $CO_2$ and oxidation of acetylene. However, this catalyst sample did not show any catalyst activity at a temperature of 110° C., which is noticeably higher than 75° C., at which fresh AgCe catalyst revealed significant activity toward selective oxidation of CO.

Example 6

The ODH process of Example 2 was used to provide the feed for this example. 1.01 g of MnCe catalyst was used for this test. The test was executed at 140° C. process temperature, 0 psig reactor outlet temperature, gas hourly space velocity of approximately 3000 h$^{-1}$. The results are summarized in the table below.

|  | $C_2H_6$ Vol.-% | $C_2H_4$ Vol.-% | $O_2$ Vol.-% | $N_2$ Vol.-% | $CO_2$ Vol.-% | CO Vol.-% | $C_2H_2$ vppm |
|---|---|---|---|---|---|---|---|
| Feed | 25.711 | 14.124 | 07582 |  51.96842 | 2.346412 | 5.091964 | 90 |
| Product | 25.55 | 14.603 | 0.32696 | 52.10005 | 2.400248 | 5.019739 | <1 |

The data show that the MnCe catalyst exhibits selective CO oxidation properties, however, it did not demonstrate any activity toward oxidation of acetylene. This catalyst sample did not show any catalytic activity at the temperature below 140° C., which is noticeably higher than 75° C., at which AgCe catalyst revealed significant activity toward selective oxidation of CO.

Example 7 (Vinyl Acetate Monomer Process)

Catalyst Preparation

A conventional palladium-gold-potassium acetate catalyst on an alumosilicate support is produced. The support particles are spherical with a diameter of approximately 5 mm and have a specific surface area of 160 to 175 m$^2$/g, a bulk density of about 600 g/l and a total pore volume of about 0.68 cm$^3$/g. The concentrations of the impregnating solutions are selected in such a manner that the finished catalyst contains about 3.3 g palladium, 1.5 g gold and 30 g potassium acetate per liter bulk volume of the catalytic support, which corresponded to a concentration of about 0.55% by weight palladium, about 0.25% by weight gold and about 5% by weight potassium acetate relative to the weight of the support used.

In a first step the support is first impregnated with a solution of potassium hydroxide. The concentration of the solution of potassium hydroxide is calculated so that after the impregnation a stoichiometric excess of potassium hydroxide on the support of about 620% is present.

After drying the catalytic supports they are impregnated with an aqueous solution of tetrachloroauric acid and potassium palladium chloride. After 20 hours the insoluble noble-metal compounds are reduced in the aqueous phase with hydrazine hydrate for a period of about 4 hours. Then the catalytic supports are washed free of chloride and dried before they are impregnated with a potassium acetate solution and redried. Before the impregnation with potassium acetate the specific surface area of the catalyst according to DIN 66 132 is about 60-70 m$^2$/g. Due to the impregnation and activation with potassium acetate the specific surface area of the catalyst declines further to 41 m$^2$/g.

The CO adsorption of the catalyst before activation is approximately 0.158 ml CO/g catalyst. The particle crush strength of the activated catalyst is about 48N (in radial measuring). The thickness of its outer shell containing noble metal is about 0.3 mm.

Vinyl Acetate Monomer Synthesis

The catalyst describer above is used in an oil-heated tubular-flow reactor (reactor length 800 mm, inner diameter 24.8 mm) at normal pressure and a space velocity (GHSV=gas hourly space velocity) of 400 h$^{-1}$ with the following gas composition: 76.0% by volume ethylene, 18.0% by volume acetic acid, 6.0% by volume oxygen.

The reactor temperature is adjusted so that the temperature in the middle of the catalytic bed is between 150° and 160° C. The resulting vinyl acetate monomer is condensed and recovered in the reactor outlet.

Example 7 (Vinyl Acetate Monomer Process—Aspen Plus® Simulation)

Aspen Plus simulation (version 9.0, Aspen Technology, Inc.) was used to simulate an experiment where acetic acid, ethylene, $O_2$ and $N_2$ were fed to a catalytic vinyl acetate reactor. The property method used was WILS-LR. The block flow diagram of this simulation is shown in FIG. 8. Simulation 800 consisted of Mixer block 810, heater block 820 and VAM reactor 830. It was assumed that ethylene feed 840, acetic acid feed 850 and a portion of $O_2$ feed 860 were provided from a product stream of a catalytic ODH ethane to ethylene reactor. A portion of $O_2$ feed 860, was provided from an external source. $N_2$ feed 870 was assumed to be representing an inert gas added to the total feed mixture to keep it outside of the flammable envelope of the acetic acid-ethylene-oxygen mixture. The following characteristics of each stream were assumed (temperature, pressure, rate, vapor fraction)

Ethylene feed 840 (120° C., 243 kPa, 24,968 Kg/hr, 100% vapor fraction) $O_2$ feed 860 (120° C., 243 kPa, 16,749 Kg/hr, 100% vapor fraction) Acetic acid feed 850 (128° C., 243 kPa, 29,426 Kg/hr, 0% vapor fraction) $N_2$ feed 870 (120° C., 243 kPa, 24,968 Kg/hr, 100% vapor fraction) Feed to preheater 880 (111° C., 243 kPa, 96,111 Kg/hr, 100% vapor fraction) Feed to VAM reactor 890 (160° C., 228 kPa, 96,111 Kg/hr, 100% vapor fraction) Product stream 900 (160° C., 193 kPa, 96,111 Kg/hr, 100% vapor fraction)

The energy/mass balance table resulted from this simulation is shown below.

The ethylene can be used to produce homopolymers, copolymers, copolymer compositions and methods of making the same. The vinyl acetate can be used to produce various materials, such as poly vinyl acetate, poly vinyl alcohol, vinyl acetate-vinyl alcohol copolymers, polyethylene-vinyl acetate copolymer, vinyl acetate-acrylic acid copolymer, polyvinyl chloride-vinyl acetate copolymer, vinylpyrrolidone-vinyl acetate copolymer, any of the above where at least a portion of the vinyl acetate repeat units are hydrolyzed to vinyl alcohol repeat units, vinyl butyral and polyvinyl butyral.

The invention claimed is:

1. A method of converting ethane to ethylene and producing vinyl acetate comprising:
   a. providing a first stream comprising ethane and oxygen to an oxidative dehydrogenation reactor;

|  |  | Stream Number | | | | | | |
| --- | --- | --- | --- | --- | --- | --- | --- | --- |
|  | Units | 850 | 840 | 880 | 870 | 860 | 900 | 890 |
| Description |  |  |  |  |  |  |  |  |
| From |  |  |  |  |  |  |  |  |
| To |  | MIXER | MIXER | MIXER PREHEAT | MIXER | MIXER | REACTOR | PREHEAT REACTOR |
| Phase |  | Liquid Phase | Vapor Phase | Vapor Phase | Vapor Phase | Vapor Phase | Vapor Phase | Vapor Phase |
| Temperature | C. | 128 | 120 | 110.5 | 120 | 120 | 160 | 160 |
| Pressure | kPa | 243 | 243 | 243 | 243 | 243 | 193 | 228 |
| Molar Vapor Fraction |  | 0 | 1 | 1 | 1 | 1 | 1 | 1 |
| Molar Liquid Fraction |  | 1 | 0 | 0 | 0 | 0 | 0 | 0 |
| Molar Enthalpy | kJ/kmol | 17259.4 | 21897.8 | −123031.0 | −387574.0 | −50331.0 | −97356.3 | −100799.0 |
| Mass Enthalpy | kJ/kg | 287.4 | 780.6 | −3577.5 | −13835.3 | −1572.9 | −2718.2 | −2931.0 |
| Mass Density | kg/cum | 930.4 | 2.1 | 2.6 | 2.1 | 2.4 | 1.9 | 2.2 |
| Enthalpy Flow | GJ/hr | 8.5 | 19.5 | −343.8 | −345.4 | −26.3 | −261.3 | −281.7 |
| Average MW |  | 60.1 | 28.1 | 34.4 | 28.0 | 32.0 | 35.8 | 34.4 |
| Mass Flows | kg/hr | 29425.8 | 24967.8 | 96110.6 | 24967.8 | 16749.1 | 96110.6 | 96110.6 |
| CO2 | kg/hr | 0.0 | 0.0 | 0.0 | 0.0 | 0.0 | 3916.9 | 0.0 |
| C2H4 | kg/hr | 0.0 | 24967.8 | 24967.8 | 0.0 | 0.0 | 17477.5 | 24967.8 |
| O2 | kg/hr | 0.0 | 0.0 | 16749.1 | 0.0 | 16749.1 | 8917.4 | 16749.1 |
| CH3COOH | kg/hr | 29425.8 | 0.0 | 29425.8 | 0.0 | 0.0 | 16064.1 | 29425.8 |
| VAM | kg/hr | 0.0 | 0.0 | 0.0 | 0.0 | 0.0 | 19155.1 | 0.0 |
| WATER | kg/hr | 0.0 | 0.0 | 0.0 | 0.0 | 0.0 | 5611.8 | 0.0 |
| N2 | kg/hr | 0.0 | 0.0 | 24967.8 | 24967.8 | 0.0 | 24967.8 | 24967.8 |
| Mass Fractions |  |  |  |  |  |  |  |  |
| CO2 |  | 0.000 | 0.000 | 0.000 | 0.000 | 0.000 | 0.041 | 0.000 |
| C2H4 |  | 0.000 | 1.000 | 0.260 | 0.000 | 0.000 | 0.182 | 0.260 |
| O2 |  | 0.000 | 0.000 | 0.174 | 0.000 | 1.000 | 0.093 | 0.174 |
| CH3COOH |  | 1.000 | 0.000 | 0.306 | 0.000 | 0.000 | 0.167 | 0.306 |
| VAM |  | 0.000 | 0.000 | 0.000 | 0.000 | 0.000 | 0.199 | 0.000 |
| WATER |  | 0.000 | 0.000 | 0.000 | 0.000 | 0.000 | 0.058 | 0.000 |
| N2 |  | 0.000 | 0.000 | 0.260 | 1.000 | 0.000 | 0.260 | 0.260 |

The data show that vinyl acetate monomer (VAM) is produced in the process.

While the present disclosure has been particularly set forth in terms of specific embodiments thereof, it will be understood in view of the instant disclosure that numerous variations upon the disclosure are now enabled yet reside within the scope of the disclosure. Accordingly, the disclosure is to be broadly construed and limited only by the scope and spirit of the claims now appended hereto.

INDUSTRIAL APPLICABILITY

The present disclosure relates to converting alkanes to alkenes, especially ethane to ethylene, with acetic acid as a byproduct of a first process. Aspects of the disclosure relate to producing vinyl acetate from the ethylene and acetic acid produced from the first process in a second or serial process.

b. converting at least a portion of the ethane to ethylene and acetic acid in the oxidative dehydrogenation reactor to provide a second stream exiting the oxidative dehydrogenation reactor comprising ethane, ethylene, acetic acid, oxygen and carbon monoxide;

c. separating at least a portion of the acetic acid from the second stream to provide an acetic acid containing stream and a third stream comprising ethane, ethylene, oxygen and carbon monoxide;

d. separating at least a portion of the third stream to provide a C2/C2+ hydrocarbons stream and an overhead stream comprising C1 hydrocarbons;

e. separating oxygen from the overhead stream, and sending an oxygen enhanced recycle stream to the oxidative dehydrogenation reactor;

f. providing the third stream to a CO Oxidation Reactor containing a catalyst comprising a group 11 metal and optionally a promoter comprising CeO$_2$, ZrO$_2$ and combinations thereof to convert a least a portion of the carbon monoxide to carbon dioxide and reacting any acetylene in the third stream to produce a fourth stream comprising ethane, ethylene and carbon dioxide; and g. providing a portion of the fourth stream and at least a portion of the acetic acid containing stream to a third reactor containing a catalyst comprising a metal selected from the group 10 and group 11 metals and combinations thereof to convert a least a portion of the ethylene and acetic acid to vinyl acetate.

2. A chemical complex for oxidative dehydrogenation of ethane and production of vinyl acetate monomer, the chemical complex comprising in cooperative arrangement:

i) at least one oxidative dehydrogenation reactor, comprising an oxidative dehydrogenation catalyst and designed to accept, in the presence of an inert diluent, an oxygen containing gas and an ethane containing gas, and to produce a product stream comprising ethylene, acetic acid, oxygen and carbon monoxide;

ii) a quench tower for quenching the product stream and for generating an acetic acid stream comprising acetic acid and an ethylene product stream comprising ethylene, carbon monoxide and oxygen;

iii) a distillation tower for separating at least a portion of the ethylene product stream into a C2/C2+ stream and an overhead stream;

iv) an oxygen separation module to separate oxygen from the overhead stream and form an oxygen enriched gas;

v) a carbon monoxide oxidation reactor for oxidizing carbon monoxide to carbon dioxide and eliminating acetylene in the ethylene product stream; and v) a vinyl acetate monomer (VAM) reactor configured to accept a portion of the ethylene product stream and at least a portion of the acetic acid stream and including a VAM catalyst to produce a VAM product stream comprising vinyl acetate monomer.

3. The chemical complex of claim 2 wherein the oxidative dehydrogenation catalyst comprises a mixed metal oxide chosen from:

i) catalysts of the formula:

$$Mo_aV_bTe_cNb_dPd_eO_f$$

wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to satisfy the valence state of the catalyst;

ii) catalysts of the formula:

$$Ni_gA_hB_iD_jO_f$$

wherein: g is a number from 0.1 to 0.9, in some cases from 0.3 to 0.9, in other cases from 0.5 to 0.85, in some instances 0.6 to 0.8; h is a number from 0.04 to 0.9; i is a number from 0 to 0.5; j is a number from 0 to 0.5; and f is a number to satisfy the valence state of the catalyst; A is chosen from Ti, Ta, V, Nb, Hf, W, Y, Zn, Zr, Si and Al or mixtures thereof; B is chosen from La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof; D is chosen from Ca, K, Mg, Li, Na, Sr, Ba, Cs, and Rb and mixtures thereof; and O is oxygen;

iii) catalysts of the formula:

$$MO_aE_kG_lO_f$$

wherein: E is chosen from Ba, Ca, Cr, Mn, Nb, Ta, Ti, Te, V, W and mixtures thereof; G is chosen from Bi, Ce, Co, Cu, Fe, K, Mg, V, Ni, P, Pb, Sb, Si, Sn, Ti, U, and mixtures thereof; a=1; k is 0 to 2; l=0 to 2, with the proviso that the total value of 1 for Co, Ni, Fe and mixtures thereof is less than 0.5; and f is a number to satisfy the valence state of the catalyst;

iv) catalysts of the formula:

$$V_mMo_nNb_oTe_pMe_gO_f$$

wherein: Me is a metal chosen from Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to satisfy the valence state of the catalyst; and v) catalysts of the formula:

$$MO_aV_rX_sY_tZ_uM_vO_f$$

wherein: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to satisfy the valence state of the catalyst;

vi) a mixed metal oxide having the empirical formula:

$$Mo_{6.5-7.0}V_3O_d$$

where d is a number to satisfy the valence of the oxide and vii) a mixed metal oxide having the empirical formula:

$$Mo_{6.25-7.25}V_3O_d$$

where d is a number to satisfy the valence of the oxide.

4. The chemical complex of claim 2, wherein the at least one oxidative dehydrogenation reactor comprises a single fixed bed type reactor.

5. The chemical complex of claim 2, wherein the at least one oxidative dehydrogenation reactor comprises a single fluidized bed type reactor and/or a moving bed reactor.

6. The chemical complex of claim 2, wherein the at least one oxidative dehydrogenation reactor comprises a swing bed type reactor arrangement.

7. The chemical complex of claim 2, wherein the at least one oxidative dehydrogenation reactor comprises more than one oxidative dehydrogenation reactor, each comprising the same or different oxidative dehydrogenation catalyst, connected in series, and wherein the product stream from each oxidative dehydrogenation reactor except the last oxidative dehydrogenation reactor in the series is fed into a downstream oxidative dehydrogenation reactor.

8. The chemical complex of claim 2, wherein the at least one oxidative dehydrogenation reactor comprises more than one oxidative dehydrogenation reactor connected in parallel and each comprising the same or different oxidative dehydrogenation catalyst.

9. The chemical complex of claim 2, wherein unreacted ethane is directed back to said at least one oxidative dehydrogenation reactor as part of the ethane containing gas.

10. The chemical complex of claim 2, wherein the carbon monoxide oxidation reactor contains a catalyst comprising a group 11 metal.

11. The chemical complex of claim 10, wherein the group 11 metal is selected from the group of copper, silver, gold and combinations thereof.

12. The chemical complex of claim 10, wherein the group 11 metal is silver or copper.

13. The chemical complex of claim 2, wherein the carbon monoxide oxidation reactor contains a catalyst comprising Ag/SiO$_2$, AgCe/SiO$_2$, AgZr/SiO$_2$, AgCeO$_2$/SiO$_2$, AgZrO$_2$/

$SiO_2$, $Cu/SiO_2$, $CuCeO_2/SiO_2$, $CuZrO_2/SiO_2$, $CuCo_3O_4/SiO_2$ and combinations thereof.

14. The chemical complex of claim 2, wherein the stream entering the carbon monoxide oxidation reactor comprises from 100 ppm to 5 wt. % oxygen.

15. The chemical complex of claim 2, wherein the stream exiting the carbon monoxide oxidation reactor is essentially free of oxygen.

16. The chemical complex of claim 2, wherein the stream exiting the carbon monoxide oxidation reactor is substantially free of acetylene.

17. The chemical complex of claim 2, wherein the amount of carbon dioxide in the stream entering the carbon monoxide oxidation reactor is less than the amount of carbon dioxide in the stream exiting the carbon monoxide oxidation reactor.

18. The chemical complex of claim 2, wherein the amount of carbon monoxide in the stream entering the carbon monoxide oxidation reactor is greater than the amount of carbon monoxide in the stream exiting the carbon monoxide oxidation reactor.

19. The chemical complex of claim 2, wherein the temperature in the carbon monoxide oxidation reactor is from 40 to 100° C.

20. The chemical complex of claim 2, wherein the VAM reactor contains a catalyst comprising a metal selected from the group 10 and group 11 metals and combinations thereof.

21. The chemical complex of claim 20, wherein the group 11 metal in the VAM reactor is selected from the group of copper, silver, gold and combinations thereof.

22. The chemical complex of claim 20, wherein the group 10 metal in the VAM reactor is selected from the group of nickel, palladium, platinum and combinations thereof.

23. The chemical complex according to claim 2, wherein a portion of the ethylene is used to make olefin derivatives.

24. The chemical complex according to claim 23, wherein the olefin derivatives are selected from polyethylene, polypropylene, ethylene oxide, propylene oxide, polyethylene oxide, polypropylene oxide, thermoplastic elastomers, thermoplastic olefins and blends and combinations thereof.

25. The chemical complex according to claim 23, wherein the portion of ethylene is used to make polyethylene.

26. The chemical complex according to claim 25, wherein the polyethylene is selected from homopolymers of ethylene, copolymers of ethylene and α-olefins, HDPE, MDPE, LDPE, LLDPE, VLDPE and combinations and blends thereof.

27. The chemical complex according to claim 25, wherein the polyethylene is produced using one or more processes selected from gas phase polyethylene processes, high pressure polyethylene processes, low pressure polyethylene processes, solution polyethylene processes, slurry polyethylene processes and combinations thereon in parallel and/or series reactor configurations.

28. A method of converting ethane to ethylene and producing vinyl acetate comprising:
   a. providing a first stream comprising ethane and oxygen to an oxidative dehydrogenation reactor;
   b. converting at least a portion of the ethane to ethylene and acetic acid in the oxidative dehydrogenation reactor to provide a second stream exiting the oxidative dehydrogenation reactor comprising ethane, ethylene, and acetic acid;
   c. separating at least a portion of the acetic acid from the second stream to provide an acetic acid containing stream and a third stream comprising ethane, and ethylene;
   d. separating at least a portion of the third stream to form an overhead stream comprising methane and oxygen;
   e. recycling an oxygen enhanced stream to the oxidative dehydrogenation reactor; and
   f. providing a portion of the third stream and at least a portion of the acetic acid containing stream to a third reactor containing a catalyst comprising a metal selected from the group 10 and group 11 metals and combinations thereof to convert a least a portion of the ethylene and acetic acid to vinyl acetate.

* * * * *